US009732068B1

(12) United States Patent
DaVanzo et al.

(10) Patent No.: US 9,732,068 B1
(45) Date of Patent: Aug. 15, 2017

(54) SYSTEM FOR CRYSTALIZING CHEMICAL COMPOUNDS AND METHODOLOGIES FOR UTILIZING THE SAME

(71) Applicant: GenSyn Technologies, Inc., Cleveland, OH (US)

(72) Inventors: Stephen P DaVanzo, Bainbridge Township, OH (US); Barry Edward Nall, Perrysville, OH (US)

(73) Assignee: GenSyn Technologies, Inc., Cleveland, OH (US)

( * ) Notice: Subject to any disclaimer, the term of this patent is extended or adjusted under 35 U.S.C. 154(b) by 418 days.

(21) Appl. No.: 14/216,188

(22) Filed: Mar. 17, 2014

Related U.S. Application Data

(60) Provisional application No. 61/788,875, filed on Mar. 15, 2013.

(51) Int. Cl.
| C30B 29/54 | (2006.01) |
| C07D 405/14 | (2006.01) |
| C07C 233/25 | (2006.01) |
| C07D 223/26 | (2006.01) |
| C07C 59/84 | (2006.01) |
| C07D 207/34 | (2006.01) |

(52) U.S. Cl.
CPC ............ C07D 405/14 (2013.01); C07C 59/84 (2013.01); C07C 233/25 (2013.01); C07D 207/34 (2013.01); C07D 223/26 (2013.01)

(58) Field of Classification Search
CPC ................................ C30B 29/54; C30B 29/56
See application file for complete search history.

(56) References Cited

U.S. PATENT DOCUMENTS

| 410,067 A | 8/1889 | Bower |
| 1,394,486 A | 10/1921 | Foster |
| 2,751,335 A | 6/1956 | Carver |

(Continued)

FOREIGN PATENT DOCUMENTS

| CN | 1718568 A | 1/2006 |
| CN | 102058539 A | 5/2011 |

(Continued)

OTHER PUBLICATIONS

DiBenedetto, G. Abstract: Precipitation of micro/nanoparticles in enhanced high energy dissipation mixing systems. ProQuest Dissertations and Theses: The Sciences and Engineering Collection 2009.

(Continued)

*Primary Examiner* — Robert M Kunemund
(74) *Attorney, Agent, or Firm* — Honigman Miller Schwarts and Cohn LLP; Douglas H. Siegel; Jonathan P. O'Brien

(57) ABSTRACT

A system including a fluid receiver defined by a crystallization chamber, three or more fluid input conduits, wherein each fluid input conduit is configured to direct a fluid into the crystallization chamber such that the fluids from the fluid input conduits converge on a single spatial coordinate (X—Y—Z) within the crystallization chamber, and a fluid outlet body portion. A process for crystallization of the chemical compound is also disclosed. Polymorphs of paracetamol, carbamazapine, ketoprofen, atorvastatin, and itraconazole also are disclosed.

33 Claims, 18 Drawing Sheets

(56) References Cited

U.S. PATENT DOCUMENTS

| | | |
|---|---|---|
| 3,364,690 A | 1/1968 | Torobin |
| 3,505,111 A | 4/1970 | Malek |
| 3,530,924 A | 9/1970 | Domning et al. |
| 4,540,602 A | 9/1985 | Motoyama et al. |
| 4,634,574 A | 1/1987 | Spurlin et al. |
| 4,675,194 A | 6/1987 | Gaffney |
| 5,074,671 A | 12/1991 | Roueche et al. |
| 5,145,684 A | 9/1992 | Liversidge et al. |
| 5,314,506 A | 5/1994 | Midler et al. |
| 5,492,654 A | 2/1996 | Kozjuk et al. |
| 5,495,872 A | 3/1996 | Gallagher et al. |
| 5,510,118 A | 4/1996 | Bosch et al. |
| 5,578,279 A | 11/1996 | Dauer et al. |
| 5,810,052 A | 9/1998 | Kozyuk |
| 5,931,771 A | 8/1999 | Kozyuk |
| 5,937,906 A | 8/1999 | Kozyuk |
| 5,969,207 A | 10/1999 | Kozyuk |
| 5,971,601 A | 10/1999 | Kozyuk |
| 6,012,492 A | 1/2000 | Kozyuk |
| 6,035,897 A | 3/2000 | Kozyuk |
| 6,211,253 B1 | 4/2001 | Marelli |
| 6,302,958 B1 | 10/2001 | Lindrud et al. |
| 6,502,979 B1 | 1/2003 | Kozyuk |
| 6,538,041 B1 | 3/2003 | Marelli |
| 6,558,435 B2 | 5/2003 | Am Ende et al. |
| 6,589,501 B2 | 7/2003 | Moser et al. |
| 6,802,639 B2 | 10/2004 | Kozyuk |
| 6,857,774 B2 | 2/2005 | Kozyuk |
| 6,869,586 B1 | 3/2005 | Moser et al. |
| 6,935,770 B2 | 8/2005 | Schueler |
| 7,041,144 B2 | 5/2006 | Kozyuk |
| 7,086,777 B2 | 8/2006 | Kozyuk |
| 7,207,712 B2 | 4/2007 | Kozyuk |
| 7,247,244 B2 | 7/2007 | Kozyuk |
| 7,314,306 B2 | 1/2008 | Kozyuk |
| 7,314,516 B2 | 1/2008 | Kozyuk |
| 7,338,551 B2 | 3/2008 | Kozyuk |
| 7,380,976 B2 | 6/2008 | Mattison et al. |
| 7,422,360 B2 | 9/2008 | Kozyuk |
| 7,708,453 B2 | 5/2010 | Kozyuk |
| 8,216,363 B2 | 7/2012 | Myerson et al. |
| 8,268,136 B2 | 9/2012 | McCutchen et al. |
| 2004/0098839 A1* | 5/2004 | Brenek ............ A61K 9/14 23/295 R |
| 2005/0202095 A1* | 9/2005 | Daiziel ............ A23J 3/16 424/489 |
| 2007/0189114 A1 | 8/2007 | Reiner et al. |
| 2008/0194868 A1 | 8/2008 | Kozyuk |
| 2010/0252660 A1 | 10/2010 | Kozyuk |
| 2011/0166352 A1* | 7/2011 | Gleeson ............ B01D 9/0009 544/363 |
| 2012/0157719 A1 | 6/2012 | Teles et al. |

FOREIGN PATENT DOCUMENTS

| | | |
|---|---|---|
| DE | 2427693 A1 | 2/1975 |
| EP | 0461930 A1 | 6/1991 |
| EP | 0461930 B1 | 9/1995 |
| EP | 2135667 A1 | 12/2009 |
| FR | 86441 E | 9/1964 |
| GB | 193979 | 3/1923 |
| GB | 1134463 A | 11/1968 |
| GB | 2398241 A | 8/2004 |
| GB | 2398241 B | 1/2005 |
| JP | 2739896 B2 | 6/1992 |
| WO | 2004/078338 A2 | 9/2004 |

OTHER PUBLICATIONS

Shi, Y. Experimental and computational investigation of turbulent mixing in microscale reactors. Iowa State University 2012.

Siddiqui, S.W. Use of the confined impinging jet reactor for production of nanoscale iron oxide particles. ProQuest Dissertations and Theses: The Sciences and Engineering Collection 2009.

Suslick, K.S. Sonochemistry. Science, vol. 247, Mar. 1990, pp. 1439-1445.

Wu, Y., et al. Features of Impinging Streams Intensifying Processes and Their Applications. International Journal of Chemical Engineering, vol. 2010, Article ID 681501, 16 pages.

Zhu, ZhengXi. Polymer Stabilized Nanosuspensions Formed Via Flash Nanoprecipitation: Nanoparticle Formation, Formulation, and Stability. Minnesota, University of Minnesota Jun. 2010.

\* cited by examiner

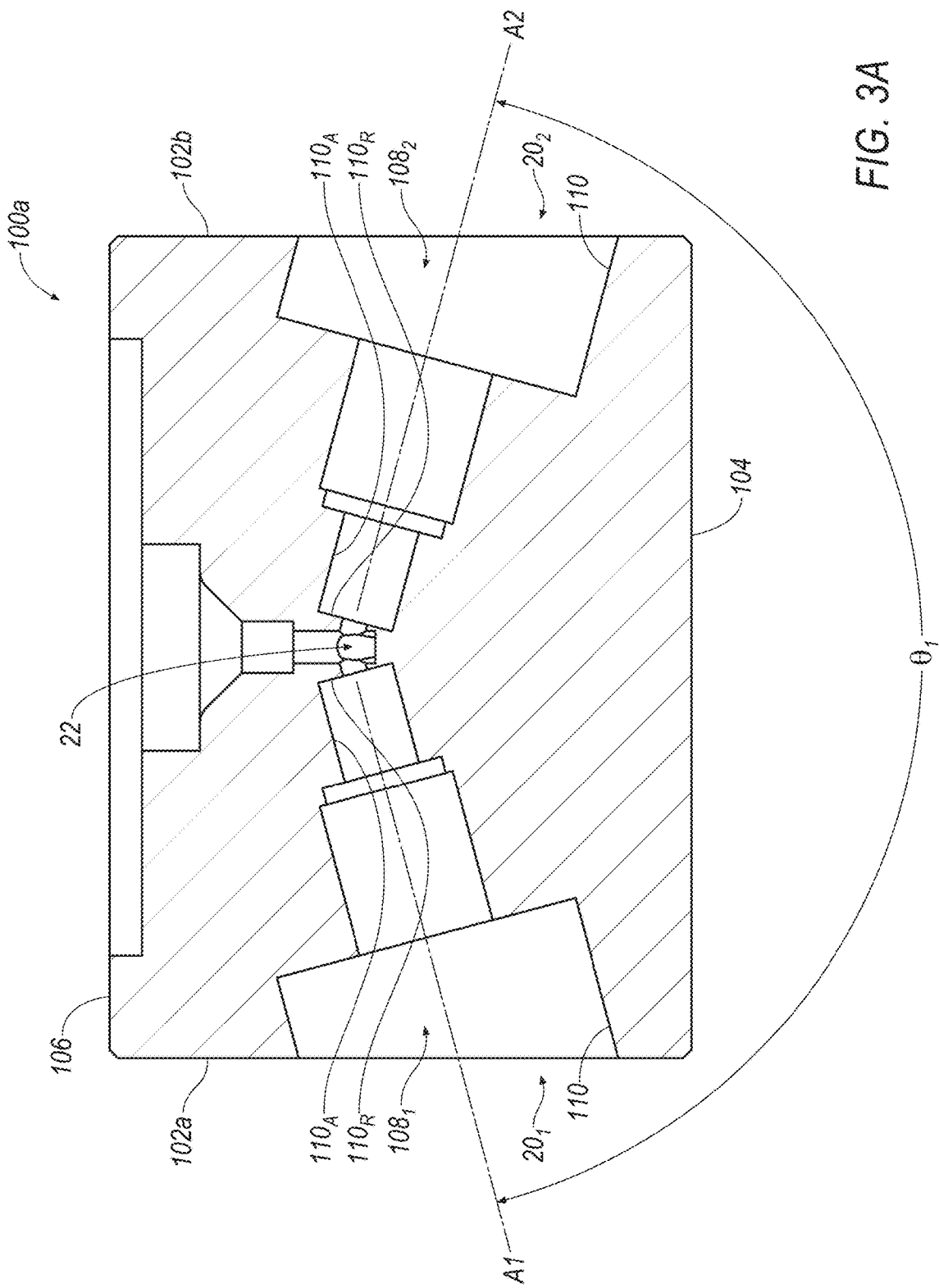

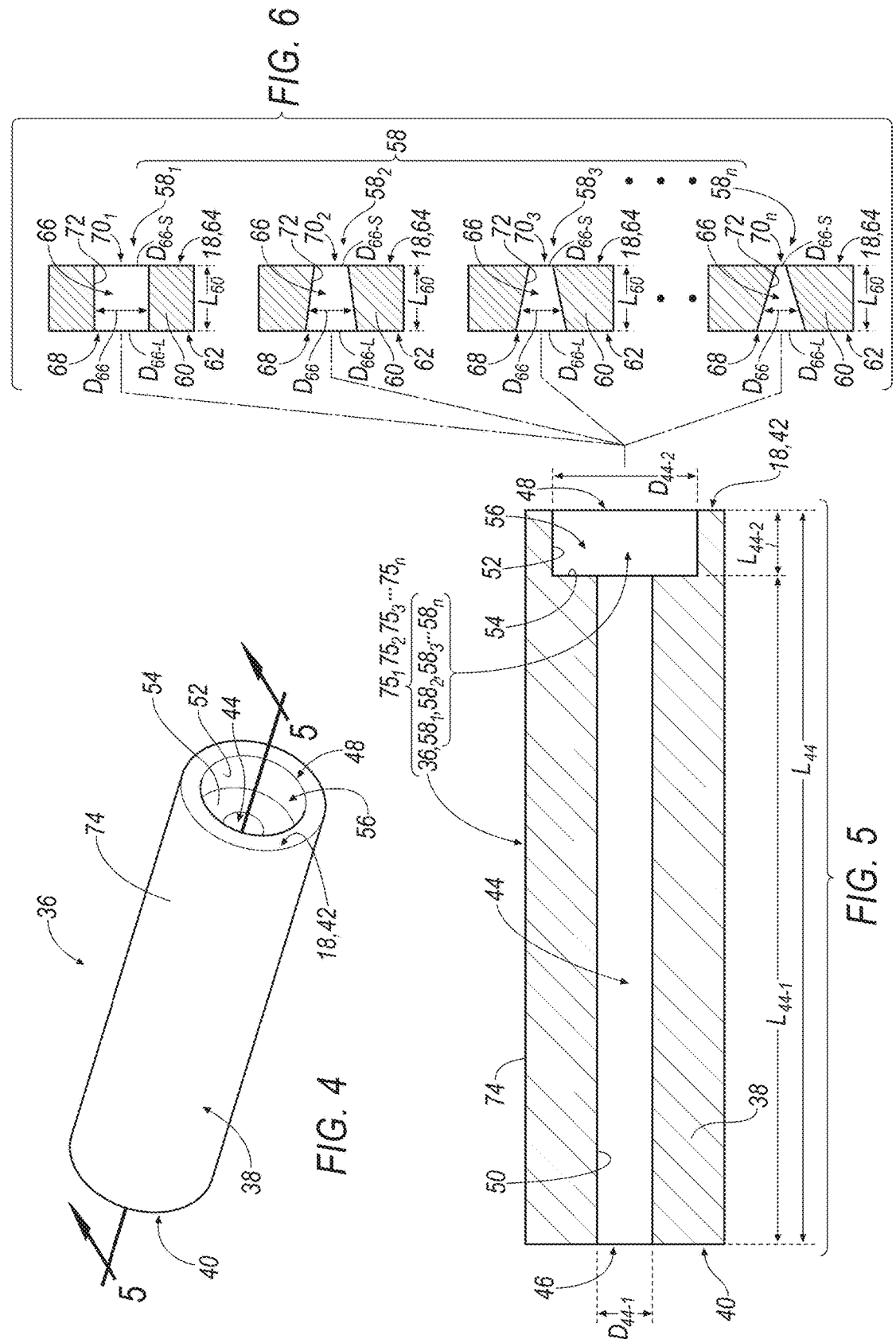

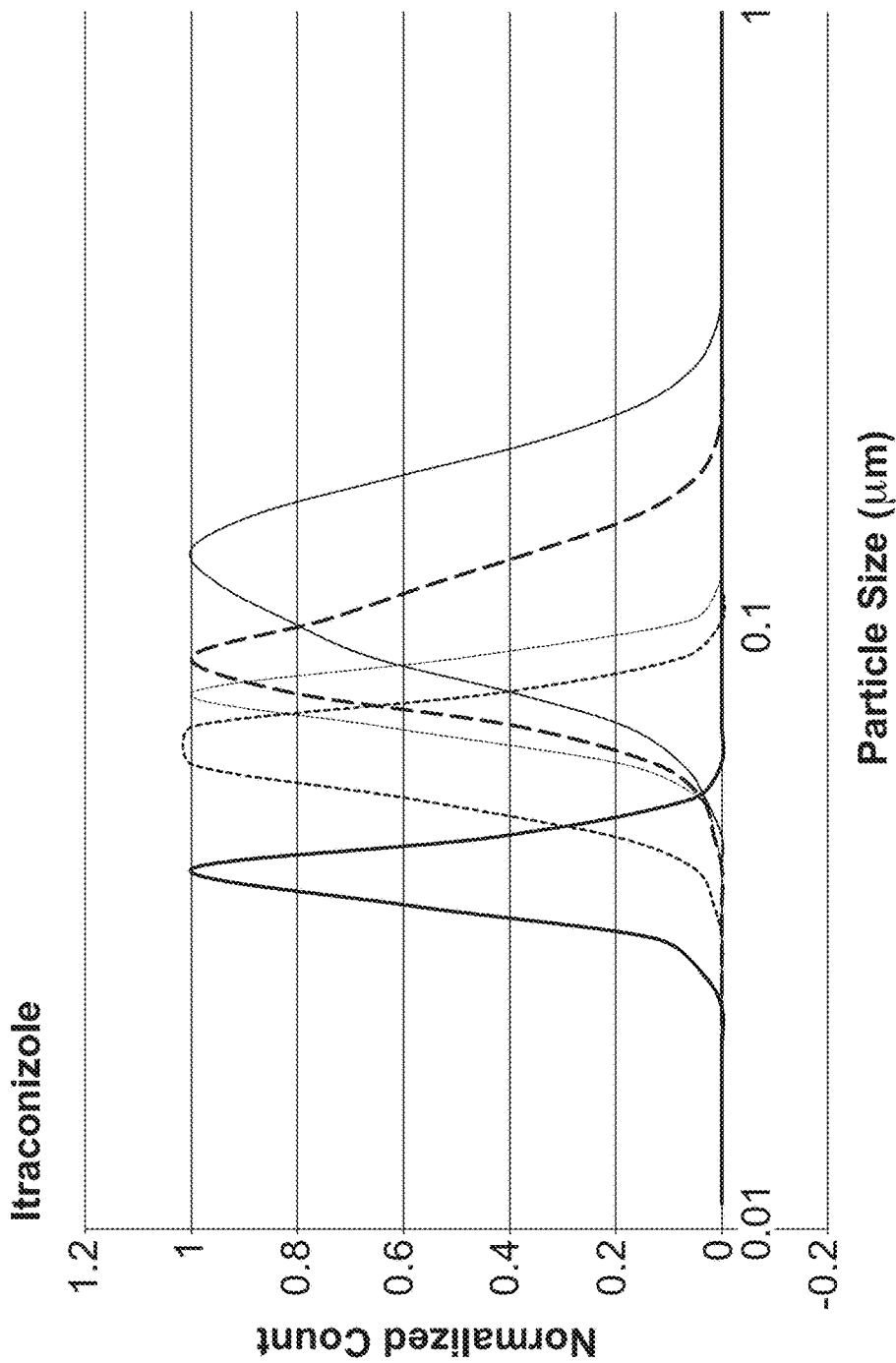

Paracetamol

Cyrstal produced by the System 10

Paracetamol

Cyrstal produced by the System 10

Ketoprofen

Cyrstal produced by the System 10

SYSTEM FOR CRYSTALIZING CHEMICAL COMPOUNDS AND METHODOLOGIES FOR UTILIZING THE SAME

CROSS-REFERENCE TO RELATED APPLICATIONS

This U.S. patent application claims priority to U.S. Provisional Application 61/788,875 filed on Mar. 15, 2013, the disclosure of which is considered part of the disclosure of this application and is hereby incorporated by reference in its entirety.

TECHNICAL FIELD

The disclosure relates to a system for crystalizing chemical compounds and methodologies for utilizing the same.

BACKGROUND

Crystallizing devices are known in the art. Even though known crystallizing devices may be suitable for their intended purpose, improvements are continuously being sought in order to advance the arts.

SUMMARY

One aspect of the disclosure provides a system that includes a fluid receiver defined by a crystallization chamber, three or more fluid input conduits, wherein each fluid input conduit is configured to direct a fluid into the crystallization chamber such that the fluids from the fluid input conduits converge on a single spatial coordinate (X—Y—Z) within the crystallization chamber, and a fluid outlet body portion.

The fluid receiver may also include a first fluid inlet port, a second fluid inlet port, a third fluid inlet port, and a fourth fluid inlet port, wherein the first fluid inlet port and the second fluid inlet port are respectively formed in opposing side surfaces of the fluid receiver, wherein the third fluid inlet port and the fourth fluid inlet port are formed in a side surface connecting the opposing side surfaces. Also, a first axis may extend through the first fluid inlet port, a second axis may extend through the second fluid inlet port, a third axis may extend through the third fluid inlet port, a fourth axis may extend through the fourth fluid inlet port, the first axis may be offset from the second axis at a first angle, the third axis may be offset from the fourth axis at a second angle, both of the first angle and the second angle may not be equal to 90°, and both of the first angle and the second angle may not be equal to 180°. In some examples, the first angle may range between about 120° and about 175° or, more specifically, the first angle may be approximately equal to 150°. In other examples, the second angle may range between about 30° and about 85° degrees or, more specifically, the second angle may be approximately equal to 60°.

In another aspect of the disclosure, the system also may include a processed fluid reservoir that is fluidly-connected to a distal end of the fluid output conduit. In another aspect of the system, each of the three or more fluid input conduits may include a proximal end that is respectively fluidly-connected to a fluid source of a plurality of fluid sources to permit the proximal end of each of the three or more fluid input conduits to respectively draw a fluid from each fluid source of the plurality of fluid sources, and a distal end that is respectively fluidly-connected to the crystallization chamber.

In a further aspect of the invention, the system also may include one or more pumps that are arranged downstream of each fluid input conduit of the three or more fluid input conduits. In another feature of the invention, each fluid input conduit of the three or more fluid input conduits may include a check valve that is arranged downstream of the pump and upstream of the distal end of each fluid conduit of the three or more fluid input conduits.

In another aspect, the invention may include a computing resource that is communicatively-coupled to each pump and that controls an operating speed of each pump to therefore control a flow rate of each fluid that is drawn from each fluid source of the plurality of fluid sources.

In some examples, of the system, each fluid input conduit of the three or more fluid input conduits may include a distal end portion having a substantially cylindrically-shaped body that defines a proximal end and a distal end, wherein the distal end of the substantially cylindrically-shaped body forms a portion of the distal end of each fluid input conduit of the three or more fluid input conduits. Further, the substantially cylindrically-shaped body of the distal end portion may form a passage that extends through an entire length of the substantially cylindrically-shaped body, wherein access to the passage may be permitted by a proximal opening formed in the proximal end of the substantially cylindrically-shaped body and a distal opening formed in the distal end of the substantially cylindrically-shaped body.

In another aspect of the invention, the proximal opening and a first substantially cylindrical inner surface of the substantially cylindrically-shaped body may define the passage to include a first diameter that extends through a majority of the length of the substantially cylindrically-shaped body, the distal opening and a second substantially cylindrical inner surface of the substantially cylindrically-shaped body may define the passage to include a second diameter that extends through a minority of the length of the substantially cylindrically-shaped body, a radial shoulder surface further may define the passage and connect the first substantially cylindrical inner surface to the second substantially cylindrical inner surface, the second diameter may be greater than the first diameter, the second substantially cylindrical inner surface and the radial shoulder surface may define the passage to include a counter bore formed in the distal end of the substantially cylindrically-shaped body In other examples, the system also may include a nozzle removably-disposed within a counter bore for removably-connecting the nozzle to the distal end of the distal end portion. And in further examples, the nozzle may include a body having a proximal end and a distal end wherein the distal end of the body of the nozzle and the distal end of the substantially cylindrically-shaped body of the distal end portion forms the distal end of each fluid input conduit of the three or more fluid input conduits. In further examples of the system, the body of the nozzle may form a passage that extends through an entire length of the body wherein access to the passage is permitted by a proximal opening formed in the proximal end of the body of the nozzle and a distal opening formed in the distal end the body of the nozzle, the passage may be formed by a substantially conical inner surface defining a diameter that decreases along the length of the body of the nozzle such that the proximal opening defines the passage to include a first, larger diameter and the distal opening defines a second, smaller diameter. In some aspects of the invention, the second, smaller diameter formed by the distal opening of the nozzle may range between about 0.001" to about 0.1".

In other examples, the system may include a fluid receiver defined by a crystallization chamber, a first fluid inlet port and a second fluid inlet port, wherein a first axis may extend through the first fluid inlet port, wherein a second axis may extend through the second fluid inlet port, wherein the first axis may be offset from the second axis at a first angle, wherein the first angle may not be equal to 90° and the first angle may not be equal to 180°; two or more fluid input conduits, wherein each fluid input conduit may be configured to direct a fluid into the crystallization chamber such that the fluids from the fluid input conduits converge on a single spatial coordinate (X—Y—Z) within the crystallization chamber, and a fluid outlet body portion.

Yet another aspect of the disclosure provides a process for crystallization of a chemical compound by using the above-described system, and that chemical compound may be a pharmaceutical compound. In some examples of the process, a first fluid of three or more fluids carried by a first fluid input conduit of the three or more fluid input conduits is a feed solution, and a second fluid, a third fluid, and a fourth fluid of the three or more fluids carried, respectively, by a second fluid input conduit, a third fluid input conduit, a fourth fluid input conduit of the three or more fluid input conduits are one or more anti-solvents. In some aspects, the feed solution may be a compound to be crystallized and one or more solvents, and the compound may be at a concentration in the solvent from about 1% to about 30% or, more specifically, the compound may be at a concentration from about 5% to about 25% or, more specifically, the compound may be at a concentration from about 10% to about 20% or, more specifically, the compound may be at a concentration from about 7% to about 8%.

In other examples, the feed solution and anti-solvents may be independently at a temperature in a range from about 0° C. to about 80° C. or, more specifically, the feed solution and anti-solvents may be independently at a temperature in a range from about 25° C. to about 60° C. Further, the feed solution or anti-solvent independently may include one or more surfactants, and those surfactants may be gelatin, casein, lecithin, gum acacia, cholesterol, steric acid, benzalkonium chloride, calcium stearate, glycerol monostearate, cetostearyl alcohol, sorbitan esters, polyoxyethylene alkyl esters, polyoxyethylene castor oil derivatives, polyoxyethylene sorbitan fatty acid esters, polyethylene glycols, polyoxyethylene stearate, sodium dodecylsulfate, hydroxyl propylcellulose, polyvinylpyrrolidone and polyvinyl alcohols, emulsifying surfactants, or soy lecithin. Additionally, in some instances, the feed solution and anti-solvents may independently run at a flow rate in a range from about 50 ml/min to about 15 l/min.

Other aspects of the disclosure include any of a polymorph of paracetamol that may have a median particle size less than about 1.3 microns, a polymorph of Carbamazapine that may have a median particle size less than about 1.5 microns, a polymorph of ketoprofen that may have a median particle size less than about 3.1 microns, a polymorph of atorvastatin that may have a median particle size less than about 126 nanometers, and a polymorph of itraconazole that may have a median particle size less than about 36 nanometers. And in some aspects the polymorph of paracetamol may have a span less than about 0.901, the polymorph of Carbamazapine may have a span less than about 0.916, the polymorph of ketoprofen may have a span less than about 1.078, the polymorph of atorvastatin may have a span less than about 0.99, or the polymorph of itraconazole may have a span less than about 0.34.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 3A is a cross-sectional view of the fluid receiver according to line 3A-3A of FIG. 2A or 2B.

FIG. 4 is a perspective view of an exemplary distal end portion of a fluid input conduit of the system of FIG. 1.

FIG. 5 is a cross-sectional view of the distal end portion of the fluid input conduit according to line 5-5 of FIG. 4.

FIG. 6 illustrates a plurality of exemplary nozzles each of which may be removably-joined with the distal end portion of a fluid input conduit of FIG. 4.

FIG. 9 is a graph illustrating several customized particles sizes and distributions of Itraconazole.

Like reference symbols in the various drawings indicate like elements.

DETAILED DESCRIPTION

Figure 1:
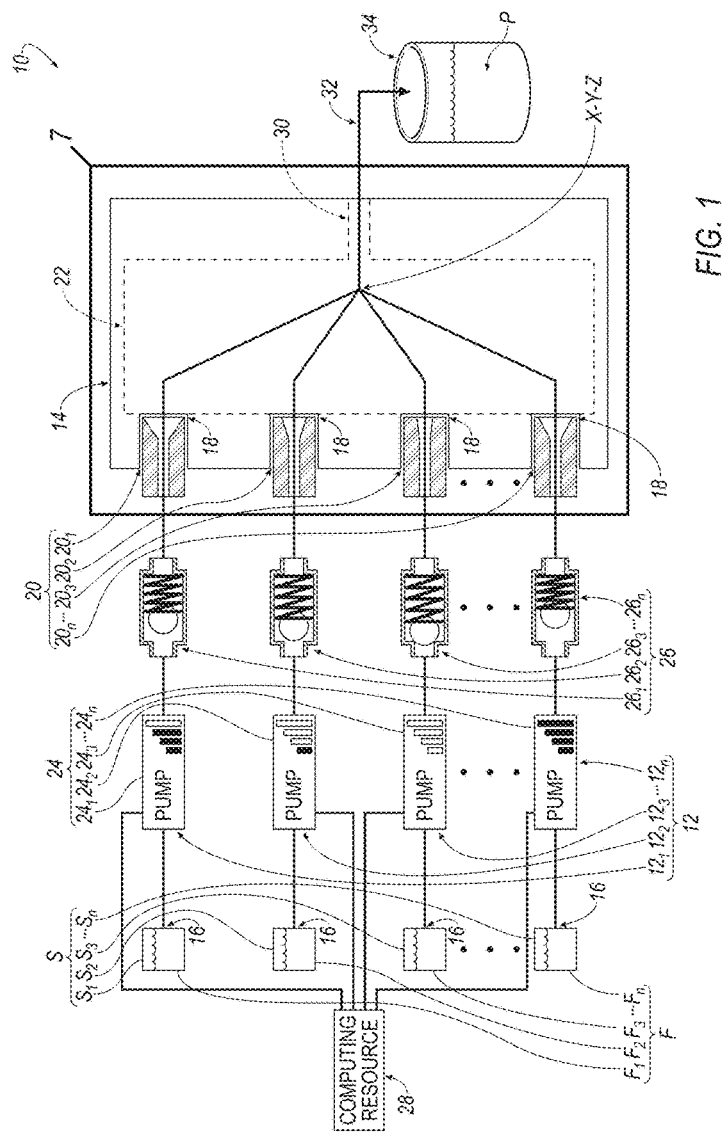
FIG. 1 is a schematic view of an exemplary system for crystalizing chemical compounds.

Referring to FIG. 1, a system for crystalizing chemical compounds is shown generally at 10. The system 10 draws a plurality of fluids, F, from a plurality of fluid sources, S, in order to produce a product, P, that is derived from two, three, or more fluids, $F_1$-$F_n$, of the plurality of fluids, F. In some instances, the plurality of fluid sources, S, containing the plurality of fluids, F, are not considered to be components of the system 10, but, rather, implements or workpieces that interface with the system 10.

As will be explained in the following disclosure, structural components of the system 10 are arranged and sized for manipulating the two, three, or more fluids, $F_1$-$F_n$, of the plurality of fluids, F, such that the more than the two fluids, $F_1$-$F_n$, of the plurality of fluids, F, undergo a 'crystallization process;' in some instances, the crystallization process performed by the system 10 may be exploited by one or more industries including, for example: the pharmaceutical industry, the fine chemical industry or the like. When utilized by the pharmaceutical industry, the system 10 may produce, for example: pharmaceutical products, P, having smaller particles that provide a higher bioavailability and shorter dissolution time; further, pharmaceutical products, P, produced by the system 10 may be defined as having, for example, improved: pharmaceutical stability, pharmaceutical purity, and pharmaceutical shelf life.

The structural components of the system 10 may include, but is not limited to: a plurality of fluid input conduits 12 that are fluidly-connected to a fluid receiver 14. The structural components of the system 10 may be made from any desirable material (e.g., stainless steel) that may be, for example, non-corrosive and durable in nature.

The plurality of fluid input conduits 12 of the exemplary system 10 includes two, three, or more fluid input conduits $12_n$ (i.e., the plurality of fluid input conduits 12 may include "n" fluid conduits so long as "n" is greater than or equal to two). As seen in the following disclosure at FIGS. 2A-2B, 3A-3B, 7 and 8A-8B, the exemplary system 10 may include four fluid conduits, such as, for example: a first fluid input conduit $12_1$, a second fluid input conduit $12_2$, a third fluid input conduit $12_3$ and a fourth fluid input conduit $12_4$ that are fluidly-connected to the fluid receiver 14.

Referring to FIG. 1, each fluid input conduit $12_1$-$12_n$ of the plurality of fluid input conduits 12 includes a proximal end 16. The proximal end 16 of each fluid input conduit $12_1$-$12_n$ of the plurality of fluid input conduits 12 is respectively fluidly-connected to a fluid source, $S_1$-$S_n$, of the plurality of fluid sources, S (e.g., the proximal end 16 of the first fluid input conduit $12_1$ is fluidly-connected to a first fluid source, $S_1$, and, the proximal end 16 of the second fluid input conduit $12_2$ is fluidly-connected to a second fluid source, $S_2$, and, the proximal end 16 of the third fluid input conduit $12_3$ is fluidly-connected to a third fluid source, $S_3$, and, the proximal end 16 of the "$n^{th}$" fluid input conduit $12_n$ is fluidly-connected to an "$n^{th}$" fluid source, $S_n$), in order to permit the proximal end 16 of each fluid input conduit $12_1$-$12_n$ of the plurality of fluid input conduits 12 to respectively draw each fluid, $F_1$-$F_n$, of the plurality of fluids, F, from each fluid source, $S_1$-$S_n$, of the plurality of fluid sources, S (e.g., the proximal end 16 of the first fluid input conduit $12_1$ draws a first fluid, $F_1$, from the first fluid source $S_1$, and, the proximal end 16 of the second fluid input conduit $12_2$ draws a second fluid, $F_2$, from the second fluid source $S_2$, and, the proximal end 16 of the third fluid input conduit $12_3$ draws a third fluid, $F_3$, from the third fluid source $S_3$, and, the proximal end 16 of the "$n^{th}$" fluid input conduit $12_n$ draws an "$n^{th}$" fluid, $F_n$, from the "$n^{th}$" fluid source $S_n$).

With continued reference to FIG. 1, each fluid input conduit $12_1$-$12_n$ of the plurality of fluid input conduits 12 includes a distal end 18. In some instances, any component (such as, e.g., structure identified at references numerals $24_1$, $24_2$, $24_3$, $24_n$, $26_1$, $26_2$, $26_3$, $26_n$, $36_1$, $36_2$, $36_3$, $36_n$, $58_1$, $58_2$, $58_3$, $58_n$) located between the proximal end 16 and the distal end 18 may constitute a portion of each fluid input conduit $12_1$-$12_n$. The distal end 18 of each fluid input conduit $12_1$-$12_n$ of the plurality of fluid input conduits 12 is disposed within and respectively fluidly-connected to a fluid inlet port $20_1$-$20_n$ of a plurality of fluid inlet ports 20 formed by the fluid receiver 14. The plurality of fluid inlet ports 20 of the exemplary fluid receiver 14 includes two, three, or more fluid inlet ports $20_n$ (i.e., the plurality of fluid inlet ports 20 may include "n" fluid inlet ports so long as "n" is greater than or equal to three). As seen in the following disclosure at FIGS. 2, 2A-2B, 3A-3B, 7 and 8A-8B, the exemplary fluid receiver 14 may include four fluid inlet ports, such as, for example: a first fluid inlet port $20_1$, a second fluid inlet port $20_2$, a third fluid inlet port $20_3$ and a fourth fluid inlet port $20_4$ that respectively receive the distal end 18 of the first fluid input conduit $12_1$, the second fluid input conduit $12_2$, the third fluid input conduit $12_3$ and the fourth fluid input conduit $12_4$.

As seen in FIG. 1, the plurality of fluid inlet ports 20 formed by the fluid receiver 14 permits the plurality of fluid input conduits 12 to fluidly connect each fluid source, $S_1$-$S_n$, of the plurality of fluid sources, S, with the fluid receiver 14 such that each fluid, $F_1$-$F_n$, of the plurality of fluids, F, may be transported from each fluid source, $S_1$-$S_n$, of the plurality of fluid sources, S, to a fluid mixing and crystallization chamber 22 formed by the fluid receiver 14. The fluid mixing and crystallization chamber 22 is fluidly connected to each fluid inlet port $20_1$-$20_n$ of the plurality of fluid inlet ports 20 formed by the fluid receiver 14. Therefore, upon interfacing the distal end 18 of each fluid input conduit $12_1$-$12_n$ of the plurality of fluid input conduits 12 with each fluid inlet port $20_1$-$20_n$ of the plurality of fluid inlet ports 20 formed by the fluid receiver 14, the fluid mixing and crystallization chamber 22 is fluidly-connected to each fluid source, $S_1$-$S_n$, of the plurality of fluid sources, S, such that each fluid, $F_1$-$F_n$, of the plurality of fluids, F, may be transported from each fluid source, $S_1$-$S_n$, of the plurality of fluid sources, S, to the fluid mixing and crystallization chamber 22.

Referring to FIG. 1, a plurality of pumps is shown generally at 24. Each fluid input conduit $12_1$-$12_n$ of the plurality of fluid input conduits 12 may include a pump $24_1$-$24_n$ of the plurality of pumps 24. Each pump $24_1$-$24_n$ may be arranged downstream of each fluid source, $S_1$-$S_n$, associated with each fluid input conduit $12_1$-$12_n$.

With continued reference to FIG. 1, a plurality of check valves are shown generally at 26. Each fluid input conduit $12_1$-$12_n$ of the plurality of fluid input conduits 12 may include a check valve $26_1$-$26_n$ of the plurality of check valves 26. Each check valve $26_1$-$26_n$ may be arranged downstream of each pump, $24_1$-$24_n$, and upstream of each distal end 18 of each fluid input conduit $12_1$-$12_n$.

As seen in FIG. 1, a computing resource is shown generally at 28. The computing resource 28 may include, but is not limited to: one or more processors or central processing units (CPUs) in communication with one or more storage resources (e.g., memory, flash memory, dynamic random access memory (DRAM), phase change memory (PCM), and/or disks having spindles)). The computing resource 28 may be communicatively-coupled (e.g., wirelessly or hardwired) to each pump $24_1$-$24_n$ of the plurality of pumps 24 in order to, for example, control the speed of each pump $24_1$-$24_n$ of the plurality of pumps 24, and, therefore, a flow rate/amount of each fluid, $F_1$-$F_n$, of the plurality of fluids, F, that is transported from each fluid source, $S_1$-$S_n$, of the plurality of fluid sources, S, to the fluid mixing and crystallization chamber 22 formed by the fluid receiver 14.

The 'crystallization process' may take place upon arrival of the two, three, or more fluids, $F_1$-$F_n$, of the plurality of fluids, F, within the fluid mixing and crystallization chamber 22. In some instances, the crystallization process takes place upon the two, three, or more fluids, $F_1$-$F_n$, of the plurality of fluids, F, being directed toward and converging upon a single spatial coordinate (i.e., an X—Y—Z spatial coordinate) within the fluid mixing and crystallization chamber 22.

After the two, three, or more fluids, $F_1$-$F_n$, of the plurality of fluids, F, have been directed into the fluid mixing and crystallization chamber 22 and converged upon the single spatial coordinate, X—Y—Z, the processed fluid, P, of the two, three, or more fluids, $F_1$-$F_n$, is then evacuated from the fluid mixing and crystallization chamber 22 at a fluid outlet port 30 formed by the fluid receiver 14. A fluid output conduit 32 is fluidly-connected to the fluid outlet port 30 for transporting the processed fluid, P, from the fluid outlet port 30 to a processed fluid reservoir 34 that received the processed fluid, P, from the fluid receiver 14.

Referring to FIGS. 4-5, an exemplary distal end portion of each fluid input conduit $12_1$-$12_n$ of the plurality of fluid input conduits 12 is shown generally at 36. The distal end portion 36 may include a substantially cylindrically-shaped body 38 having a proximal end 40 and a distal end 42; the distal end 42 of the substantially cylindrically-shaped body 38 may also define a portion of the distal end 18 of each fluid input conduit $12_1$-$12_n$ of the plurality of fluid input conduits 12.

The distal end portion 36 forms a passage 44 that extends through an entire length, $L_{44}$ (see, e.g., FIG. 5), of the substantially cylindrically-shaped body 38 from the proximal end 40 of the substantially cylindrically-shaped body 38 to the distal end 42 of the substantially cylindrically-shaped body 38. Access to the passage 44 is permitted by a proximal opening 46 (see, e.g., FIG. 5) formed in the proximal end 40 of the substantially cylindrically-shaped body 38 and a distal opening 48 formed in the distal end 42 of the substantially cylindrically-shaped body 38.

The proximal opening 46 and a first substantially cylindrical inner surface 50 of the substantially cylindrically-shaped body 38 generally defines the passage 44 to include a first diameter, $D_{44-1}$ (see, e.g., FIG. 5), that extends through a majority, $L_{44-1}$ (see, e.g., FIG. 5), of the length, $L_{44}$, of the substantially cylindrically-shaped body 38. The distal opening 48 and a second substantially cylindrical inner surface 52 of the substantially cylindrically-shaped body 38 generally defines the passage 44 to include a second diameter, $D_{44-2}$, that extends through a minority, $L_{44-2}$, of the length, $L_{44}$, of the substantially cylindrically-shaped body 38. A radial shoulder surface 54 further defines the passage 44 and connects the first substantially cylindrical inner surface 50 to the second substantially cylindrical inner surface 52. In some examples, the second diameter, $D_{44-2}$, that extends through a minority, $L_{44-2}$, of the length, $L_{44}$, of the substantially cylindrically-shaped body 38 is greater than the first diameter, $D_{44-1}$, that extends through a majority, $L_{44-1}$, of the length, $L_{44}$, of the substantially cylindrically-shaped body 38.

The second substantially cylindrical inner surface 52 and the radial shoulder surface 54 generally defines the passage 44 to include a substantially cylindrically-shaped counter bore 56 formed in the distal end 42 of the substantially cylindrically-shaped body 38. A nozzle $58_1$, $58_2$, $58_3$, $58_n$ (see, e.g., FIG. 6) may be removably-disposed within the substantially cylindrically-shaped counter bore 56 in order to permit the nozzle $58_1$, $58_2$, $58_3$, $58_n$ to be removably-connected to the distal end 42 of the distal end portion 36 of each fluid input conduit $12_1$-$12_n$ of the plurality of fluid input conduits 12.

Referring to FIG. 6, a plurality of exemplary nozzles is shown generally at 58. Each nozzle $58_1$, $58_2$, $58_3$, $58_n$ of the plurality of exemplary nozzles 58 may include a substantially cylindrically-shaped body 60 having a proximal end 62 and a distal end 64; the distal end 64 of the substantially cylindrically-shaped body 60 may also define a portion of the distal end 18 of each fluid input conduit $12_1$-$12_n$ of the plurality of fluid input conduits 12. Each nozzle $58_1$, $58_2$, $58_3$, $58_n$ forms a passage 66 that extends through an entire length, $L_{60}$, of the substantially cylindrically-shaped body 60 from the proximal end 62 of the substantially cylindrically-shaped body 60 to the distal end 64 of the substantially cylindrically-shaped body 60. Access to the passage 66 is permitted by a proximal opening 68 formed in the proximal end 62 of the substantially cylindrically-shaped body 60 and a distal opening $70_1$, $70_2$, $70_3$, $70_n$ formed in the distal end 64 of the substantially cylindrically-shaped body 60.

The passage 66 of each nozzle $58_1$, $58_2$, $58_3$, $58_n$ may be formed by an inner surface 72, e.g., the inner surface 72 is conical. The passage 66 includes a diameter, $D_{66}$, that may decrease along the length, $L_{60}$, as each nozzle $58_1$, $58_2$, $58_3$, $58_n$ extends from the proximal end 62 of the substantially cylindrically-shaped body 60 toward the distal end 64 of the substantially cylindrically-shaped body 60.

Because the diameter, $D_{66}$, may decrease along the length, $L_{60}$, as each nozzle $58_1$, $58_2$, $58_3$, $58_n$ extends from the proximal end 62 to the distal end 64, the proximal opening 68 generally defines the passage 66 to include a first, larger diameter, $D_{66-L}$, and, the distal opening $70_1$, $70_2$, $70_3$, $70_n$ generally defines the passage 66 to include a second, smaller diameter, $D_{66-S}$. In some instances, the first, larger diameter, $D_{66-L}$, formed by the proximal opening 68 of the nozzle $58_1$, $58_2$, $58_3$, $58_n$ may be substantially similar to the first diameter, $D_{44-1}$, formed by the passage 44 of the substantially cylindrically-shaped body 38 of the distal end portion 36.

As seen in FIG. 6, comparatively, the second, smaller diameter, $D_{66-S}$, of each nozzle $58_1$, $58_2$, $58_3$, $58_n$ has a unique size. For example, the diameter, $D_{66-S}$, of formed by the distal opening $70_1$ of the nozzle $58_1$ is larger than the diameter, $D_{66-S}$, of formed by the distal opening $70_2$ of the nozzle $58_2$, and, the diameter, $D_{66-S}$, of formed by the distal opening $70_2$ of the nozzle $58_2$ is larger than the diameter, $D_{66-S}$, of formed by the distal opening $70_3$ of the nozzle $58_3$, and, the diameter, $D_{66-S}$, of formed by the distal opening $70_3$ of the nozzle $58_3$ is larger than the diameter, $D_{66-S}$, of formed by the distal opening $70_n$ of the nozzle $58_n$.

Each diameter, $D_{66-S}$, formed by the distal opening $70_1$, $70_2$, $70_3$, $70_n$ of each nozzle $58_1$, $58_2$, $58_3$, $58_n$ yields a different flow rate of the fluid, $F_1$-$F_n$, that is directed into the fluid mixing and crystallization chamber 22 formed by the fluid receiver 14. Therefore, upon determining a desired flow rate provided by a particle nozzle $58_1$, $58_2$, $58_3$, $58_n$, a user of the system 10 may be permitted to select and subsequently removably-deposit the selected nozzle $58_1$, $58_2$, $58_3$, $58_n$ of the plurality of nozzles 58 within the substantially cylindrically-shaped counter bore 56 formed in the distal end 42 of the substantially cylindrically-shaped body 38 of the distal end portion 36 of each fluid input conduit $12_1$-$12_n$ of the plurality of fluid input conduits 12.

In some instances, each diameter, $D_{66-S}$, formed by the distal opening $70_1$, $70_2$, $70_3$, $70_n$ of each nozzle $58_1$, $58_2$, $58_3$, $58_n$ may be independently sized to range between about 0.001" to about 0.1". In other instances, each diameter, $D_{66-S}$, formed by the distal opening $70_1$, $70_2$, $70_3$, $70_n$ of each nozzle $58_1$, $58_2$, $58_3$, $58_n$ may be independently sized to range between about 0.002" to about 0.2". In other embodiments, each diameter, $D_{66\text{-}S}$, formed by the distal opening $70_1$, $70_2$, $70_3$, $70_n$ of each nozzle $58_1$, $58_2$, $58_3$, $58_n$ may be independently sized to range between about 0.004" to about 0.008".

Referring to FIG. 5, upon disposing a selected nozzle $58_1$, $58_2$, $58_3$, $58_n$ of the plurality of nozzles 58 within the cylindrically-shaped counter bore 56, the selected nozzle $58_1$, $58_2$, $58_3$, $58_n$ and the distal end portion 36 may form a subassembly $75_1$, $75_2$, $75_3$, $75_n$. The subassembly $75_1$, $75_2$, $75_3$, $75_n$ may be referred to as a "controlled flow cavitation device." Collectively, the distal ends 42, 64 of the distal end portion 36 and the selected nozzle $58_1$, $58_2$, $58_3$, $58_n$ define the distal end 18 of each fluid input conduit $12_1$-$12_n$ of the plurality of fluid input conduits 12.

Figure 2:
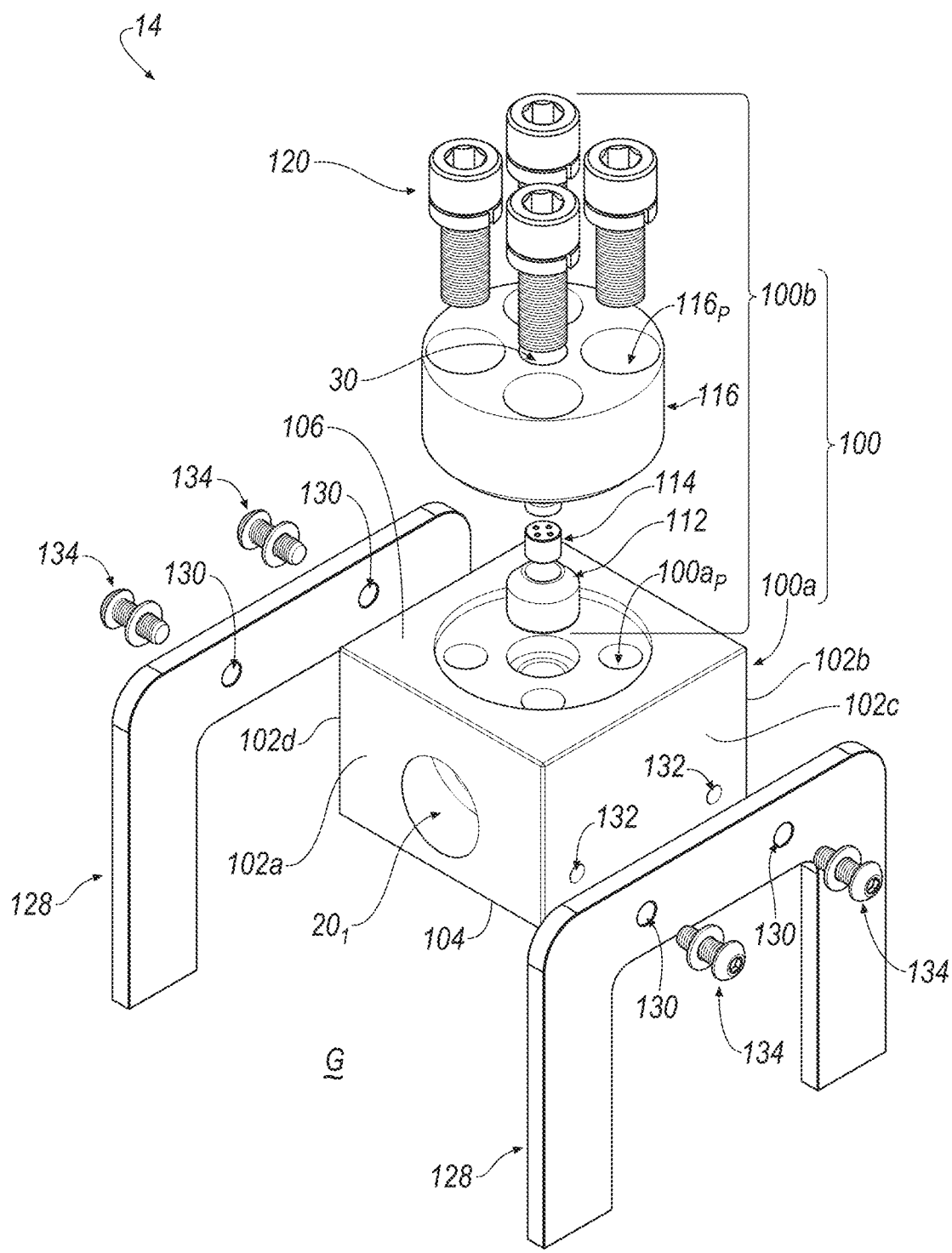
FIG. 2 is a top exploded view of an exemplary fluid receiver of the system of FIG. 1.
Figure 7:
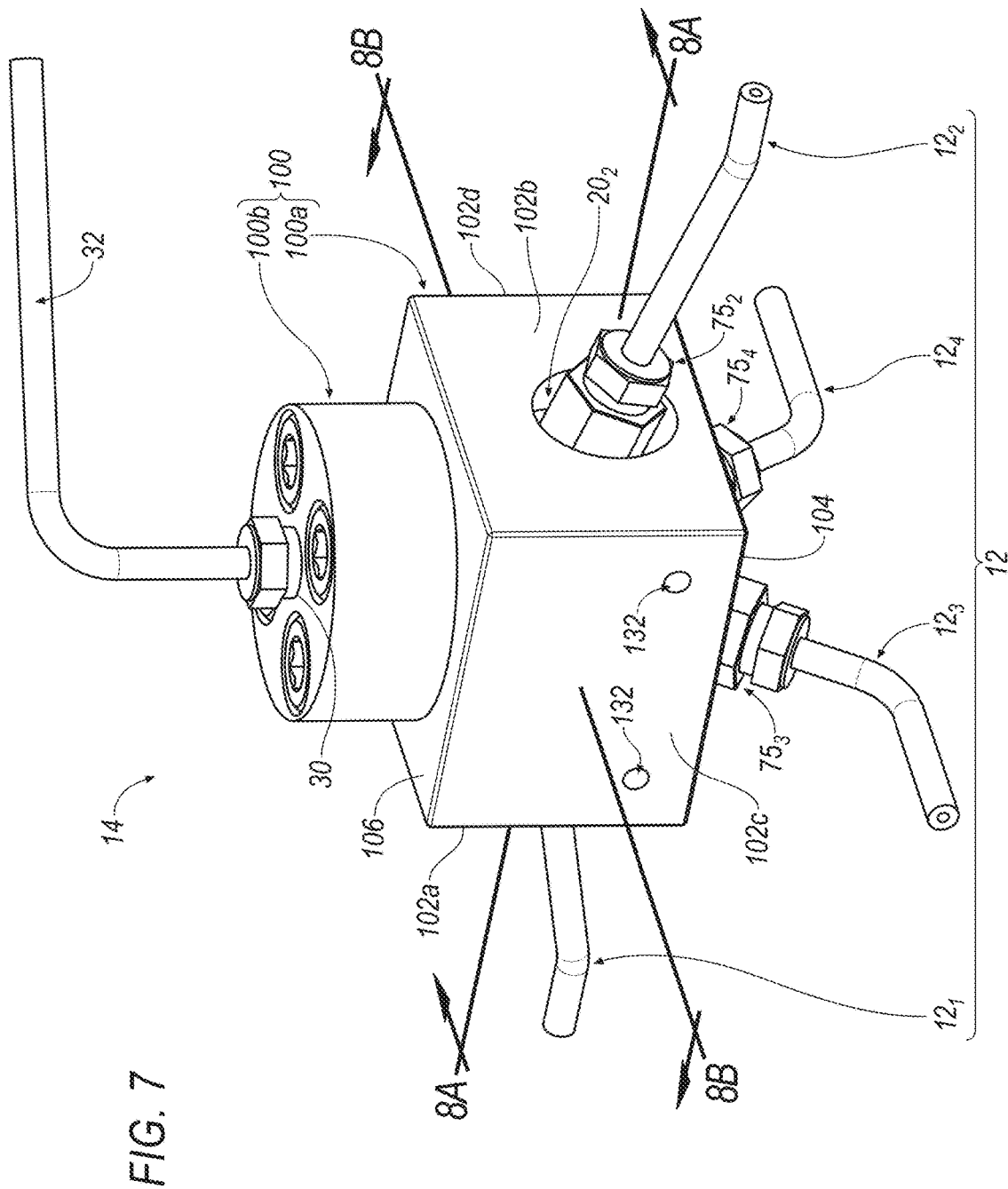
FIG. 7 is a perspective view of an exemplary system for crystalizing chemical compounds according to line 7 of FIG. 1.

Referring to FIGS. 2 and 7, an exemplary fluid receiver 14 of an exemplary system 10 is shown. Although the fluid receiver 14 shown and described at FIGS. 2 and 7 as including a plurality of components, the receiver 14 is not limited to the plurality of components or a particular shape, size or geometry. In some instances, the exemplary fluid receiver 14 shown at FIGS. 2 and 7 may include a body 100. The body 100 may include a fluid inlet body portion 100a (see also, e.g., FIGS. 2A-2B and 3A-3B) and a fluid outlet body portion 100b. The fluid inlet body portion 100a may form the plurality of fluid inlet ports 20, and, the fluid outlet body portion 100b may form the fluid outlet port 30. The plurality of fluid inlet ports 20 may include a first fluid inlet port $20_1$, a second fluid inlet port $20_2$, a third fluid inlet port $20_3$ and a fourth fluid inlet port $20_4$.

As seen in FIGS. 2 and 2A-2B and 3A-3B, an exemplary fluid inlet body portion 100a includes a substantially cube shape having four side surfaces 102a-102d a lower surface 104 and an upper surface 106. The four side surfaces 102a-102d include a first side surface 102a, a second side surface 102b, a third side surface 102c and a fourth side surface 102d. The first side surface 102a is directly opposite the second side surface 102b, and, the third side surface 102c is directly opposite the fourth side surface 102d. The lower surface 104 is directly opposite the upper surface 106.

Figure 2A:
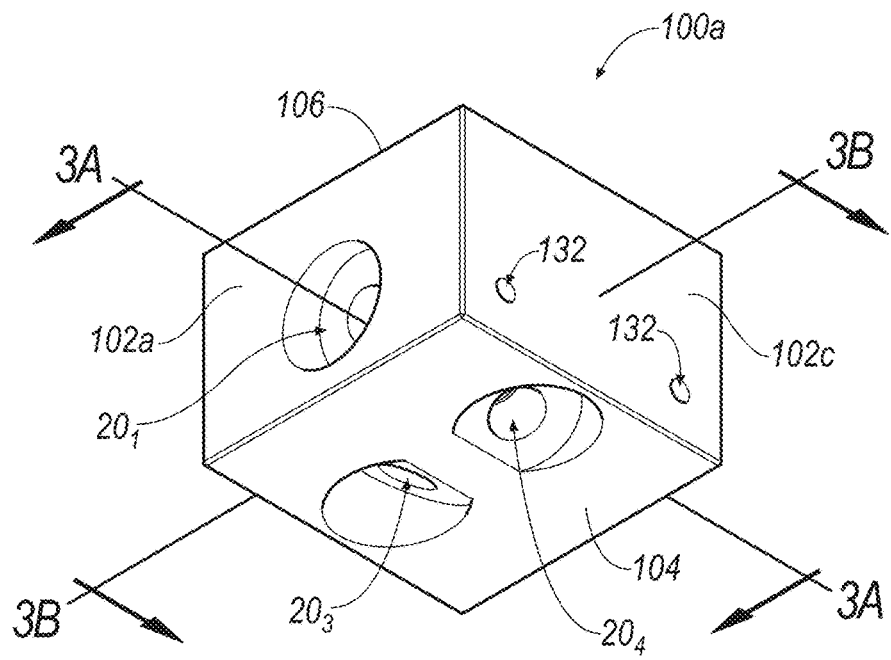
FIG. 2A is a bottom, left-side view of a portion of the exemplary fluid receiver of the FIG. 2.
Figure 2B:
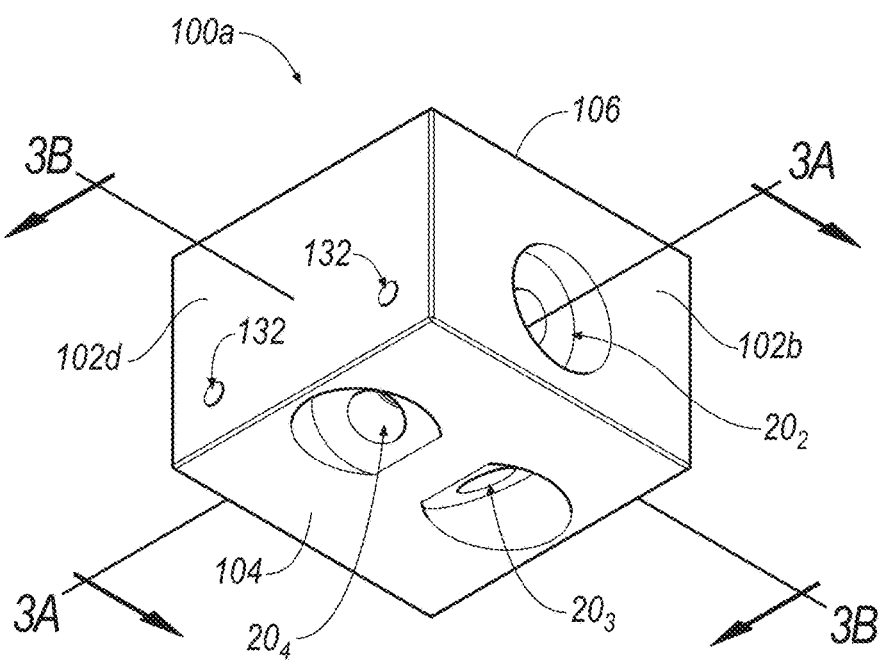
FIG. 2B is a bottom, right-side view of a portion of the exemplary fluid receiver of the FIG. 2.
Figure 3B:
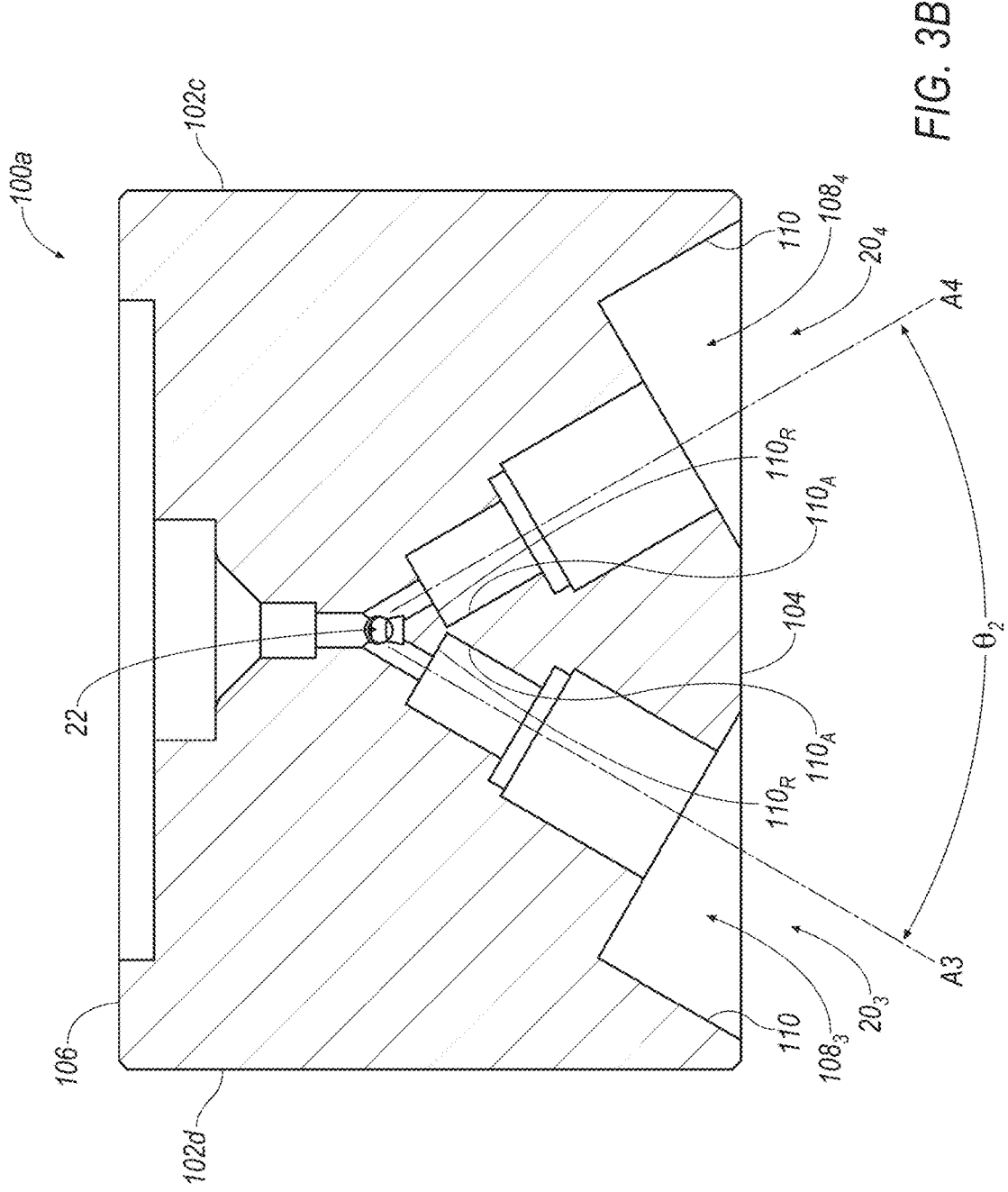
FIG. 3B is a cross-sectional view of the fluid receiver according to line 3B-3B of FIG. 2A or 2B.

Referring to FIGS. 2A and 3A, the first fluid inlet port $20_1$ of the plurality of fluid inlet ports 20 is formed by and recessed in the first side surface 102a. As seen in FIGS. 2B and 3A, the second fluid inlet port $20_2$ of the plurality of fluid inlet ports 20 is formed by and recessed in the second side surface 102b. Referring to FIGS. 2A-2B and 3B, both of the third fluid inlet port $20_3$ of the plurality of fluid inlet ports 20 and the fourth fluid inlet port $20_4$ of the plurality of fluid inlet ports 20 are formed by and recessed in the lower surface 104.

As seen in FIGS. 3A and 3B, each of the first, second, third and fourth fluid inlet ports $20_1$, $20_2$, $20_3$, $20_4$ of the plurality of fluid inlet ports 20 are, respectively, defined by a first, second, third and fourth substantially stepped counter bore $108_1$, $108_2$, $108_3$, $108_4$. Each substantially stepped counter bore $108_1$, $108_2$, $108_3$, $108_4$ is in fluid communication with the fluid mixing and crystallization chamber 22.

Each of the first, second, third and fourth stepped counter bore $108_1$, $108_2$, $108_3$, $108_4$ is defined by a stepped surface 110. As will be shown and described in the following disclosure at FIGS. 8A-8B, an outer surface portion 74 of the distal end portion 36 of the controlled flow cavitation device $75_1$, $75_2$, $75_3$, $75_4$ may be disposed adjacent an axial distal portion $110_A$ of the stepped surface 110, and, the distal end 42, 64 of each the controlled flow cavitation devices $75_1$, $75_2$, $75_3$, $75_4$ is disposed adjacent a radial distal portion $110_R$ of the stepped surface 110.

Referring to FIG. 3A, a first axis, A1-A1, extends through the first fluid inlet port $20_1$ that is formed by and recessed in the first side surface 102a. A second axis, A2-A2, extends through the second fluid inlet port $20_2$ that is formed by and recessed in the second side surface 102b. As will be explained in the following disclosure at FIG. 8A: upon insertion of the first controlled flow cavitation device $75_1$ within the first fluid inlet port $20_1$, the first controlled flow cavitation device $75_1$ is removably-fixed within the first fluid inlet port $20_1$ along the first axis, A1-A1, and, upon insertion of the second controlled flow cavitation device $75_2$ within the second fluid inlet port $20_2$, the second controlled flow cavitation device $75_2$ is removably-fixed within the second fluid inlet port $20_2$ along the second axis, A2-A2.

The first axis, A1-A1, is non-orthogonal to the second axis, A2-A2. As used herein, the term "non-orthogonal" means not at a right angle (90°), such that, as will be described in the following disclosure at FIGS. 7 and 8A-8B, a stream of a first fluid, $F_1$, supplied to the fluid mixing and crystallization chamber 22 by the first controlled flow cavitation device $75_1$ (that is disposed within the first fluid inlet port $20_1$) does not intersect at a right angle at the single spatial coordinate, X—Y—Z, with a second fluid, $F_2$, supplied to the fluid mixing and crystallization chamber 22 by the second controlled flow cavitation device $75_2$ (that is disposed within the second fluid inlet port $20_2$). Further, the first axis, A1-A1, is not arranged relative to the second axis, A2-A2, at an angle (see, e.g., the first angle θ1) equal to 180° such that, as will be described in the following disclosure at FIGS. 7 and 8A-8B, a stream of a first fluid, $F_1$, supplied to the fluid mixing and crystallization chamber 22 by the first controlled flow cavitation device $75_1$ (that is disposed within the first fluid inlet port $20_1$) does not directly oppositely impact at the single spatial coordinate, X—Y—Z, with a second fluid, $F_2$, supplied to the fluid mixing and crystallization chamber 22 by the second controlled flow cavitation device $75_2$ (that is disposed within the second fluid inlet port $20_2$).

The arrangement of the first axis, A1-A1, and the second axis, A2-A2, may be defined by a first angle, θ1. In some instances, the first angle, θ1, may range between, for example, about 120° and about 175° degrees. In other instances, the first angle, θ1, may range between about 140° and about 160°. In some implementations, the first angle, θ1, may be equal to about 150°.

Referring to FIG. 3B, a third axis, A3-A3, extends through the third fluid inlet port $20_3$ that is formed by and recessed in the lower surface 104. A fourth axis, A4-A4, extends through the fourth fluid inlet port $20_4$ that is formed by and recessed in the lower surface 104. As will be explained in the following disclosure at FIG. 8B: upon insertion of the third controlled flow cavitation device $75_3$ within the third fluid inlet port $20_3$, the third controlled flow cavitation device $75_3$ is removably-fixed within the third fluid inlet port $20_3$ along the third axis, A3-A3, and, upon insertion of the fourth controlled flow cavitation device $75_4$ within the fourth fluid inlet port $20_4$, the fourth controlled flow cavitation device $75_4$ is removably-fixed within the fourth fluid inlet port $20_4$ along the fourth axis, A4-A4.

The third axis, A3-A3, is non-orthogonal to the fourth axis, A4-A4. As used herein, the term "non-orthogonal" means not at a right angle (90°), such that, as will be described in the following disclosure at FIGS. 7 and 8A-8B, a stream of a third fluid, $F_3$, supplied to the fluid mixing and crystallization chamber 22 by the third controlled flow cavitation device $75_3$ (that is disposed within the third fluid inlet port $20_3$) does not intersect at the single spatial coordinate, X—Y—Z, at a right angle with a fourth fluid, $F_4$, supplied to the fluid mixing and crystallization chamber 22 by the fourth controlled flow cavitation device $75_4$ (that is disposed within the fourth fluid inlet port $20_4$). Further, the third axis, A3-A3, is not arranged relative to the fourth axis, A4-A4, at an angle (see, e.g., the second angle θ2) equal to 180° such that, as will be described in the following disclosure at FIGS. 7 and 8A-8B, a stream of a third fluid, $F_3$, supplied to the fluid mixing and crystallization chamber 22 by the third controlled flow cavitation device $75_3$ (that is disposed within the third fluid inlet port $20_3$) does not directly oppositely impact at the single spatial coordinate, X—Y—Z, with a fourth fluid, $F_4$, supplied to the fluid mixing and crystallization chamber 22 by the fourth controlled flow cavitation device $75_4$ (that is disposed within the fourth fluid inlet port $20_4$).

The arrangement of the third axis, A3-A3, and the fourth axis, A4-A4, may be defined by a second angle, θ2. In some instances, the second angle, θ2, may range between, for example, about 30° and about 85° degrees. In other instances, the second angle, θ2, may preferably range between about 50° and about 70°. In some implementations, the second angle, θ2, may more preferably be equal to about 60°.

In some instances, the fluid mixing and crystallization chamber 22 may include a generally tubular shape. However, the fluid mixing and crystallization chamber 22 can be configured to include any desirable shape as long as the fluid mixing and crystallization chamber 22 allows all of the first, second, third and fourth controlled flow cavitation devices $75_1$, $75_2$, $75_3$, $75_4$ to be angularly positioned at, for example, the first angle, θ1, and the second angle, θ2, such that all of the fluid streams, $F_1$-$F_4$, provided by the first, second, third and fourth controlled flow cavitation devices $75_1$, $75_2$, $75_3$, $75_4$ converge at the single spatial coordinate, X—Y—Z, at a non-orthogonal and not directly opposite manner.

Figure 8A:
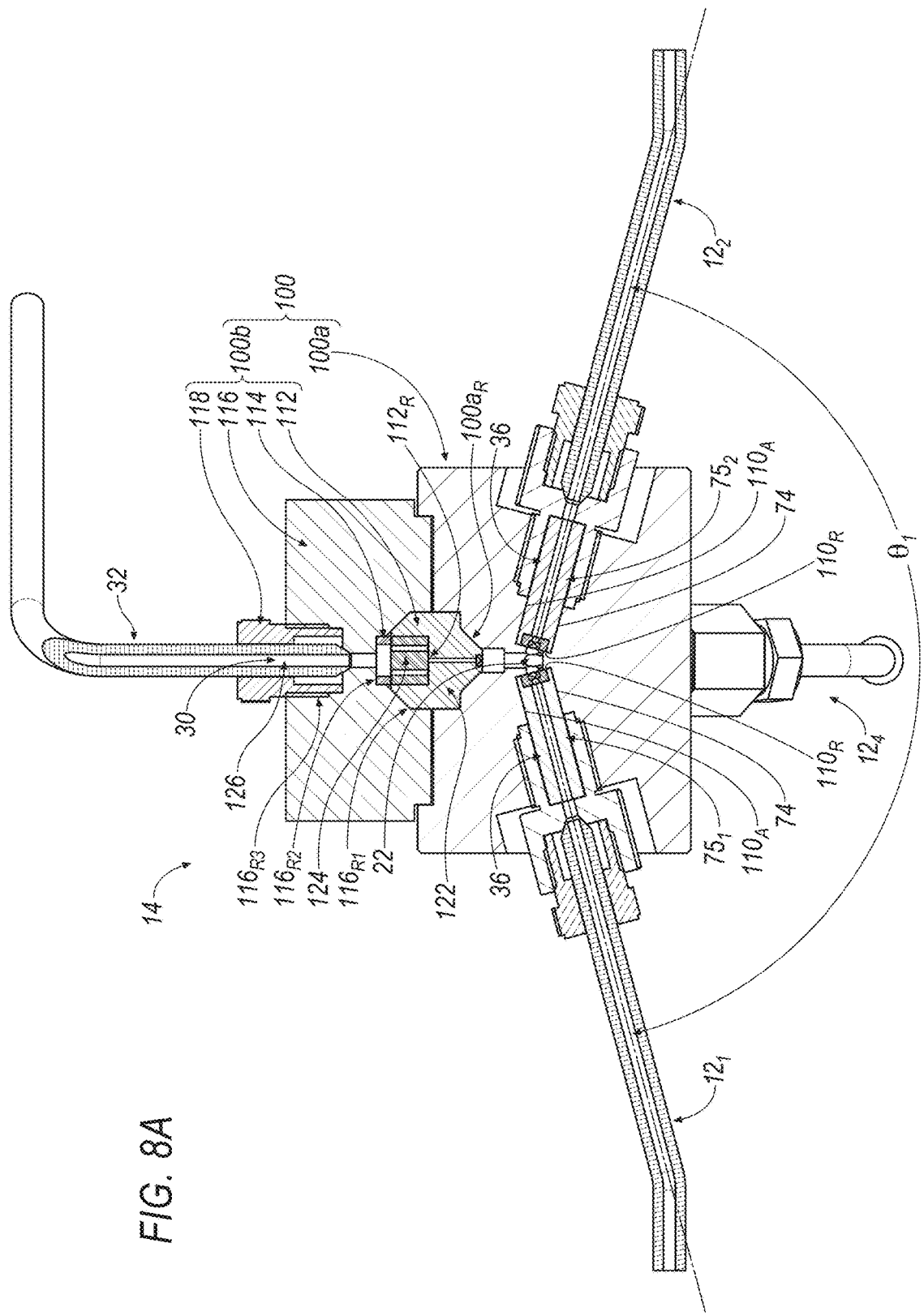
FIG. 8A is a cross-sectional view according to line 8A-8A of FIG. 7.
Figure 8B:
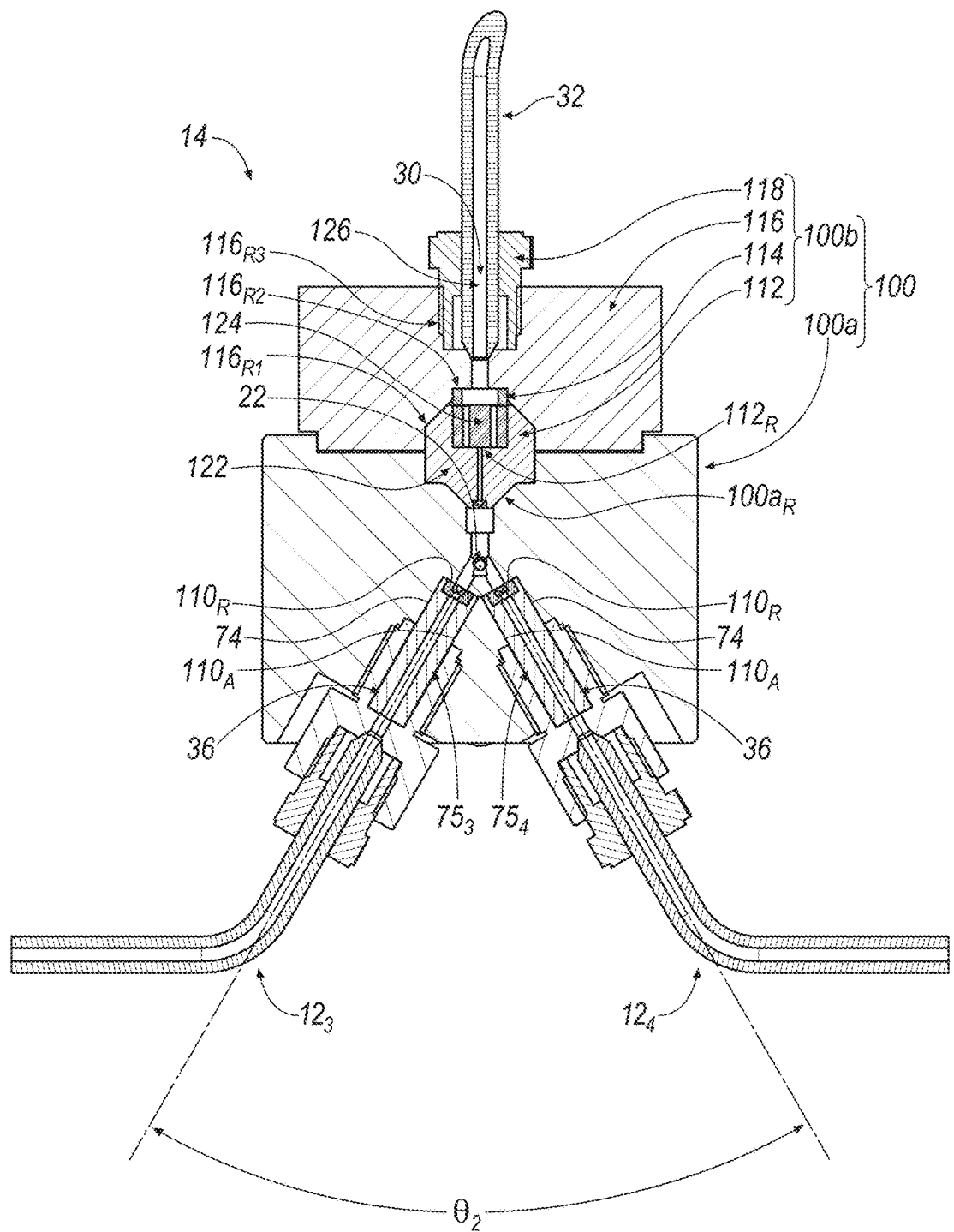
FIG. 8B is a cross-sectional view according to line 8B-8B of FIG. 7.

Referring to FIGS. 2 and 8A-8B, some implementations of the fluid outlet body portion 100b of the body 100 may include a plurality of members 112-118. Although the fluid outlet body portion 100b of the body 100 is shown at FIGS. 2 and 8A-8B as including a plurality of members 112-118, the fluid outlet body portion 100b of the body 100 is not limited to the plurality of members 112-118 or a particular shape, size or geometry. The plurality of members 112-118 may be defined by a first member 112, a second member 114, a third member 116 and a fourth member 118. As seen in FIGS. 8A-8B, each member 112-118 of the fluid outlet body portion 100b include at least one passage that permits the fluid mixing and crystallization chamber 22 to be in fluid communication with the fluid output conduit 32. Further, the at least one passage in members 112-118 of the fluid outlet body portion 100b can be used to restrict the flow of fluid out of the crystallization chamber 22. Similar to the diameter $D_{66-S}$ formed by the distal openings $70_1$, $70_2$, $70_3$, $70_n$ of each nozzle $58_1$, $58_2$, $58_3$, $58_n$, the at least one passage in members 112-118 of the fluid outlet body portion 100b has a diameter than can be sized to range from about 0.001" and 0.1". By using a different diameter size for the at least one passage in members 112-118, the flow of processed fluid, P, out of the crystallization chamber 22 can be restricted, thereby creating a condition of controlled hydraulic cavitation. For example, the passage through member 112 can be changed to control the flow of fluid out of the crystallization chamber 22 thus providing back pressure in the crystallization chamber 22. This back pressure focuses mixing of fluids $F_1$-$F_4$ away from the interior walls of the crystallization chamber 22 and into a mixing zone about the single spatial coordinate, X—Y—Z. As such, changing the size of the passage through member 112 will change the size of the mixing zone. Various structures can be used to form members 112-118 and the passage through members 112-118. For example, member 112 may be formed similar to any of nozzles $58_1$, $58_2$, $58_3$, $58_n$, having a fixed-size proximal opening and a distal opening of any of a variety of sizes. Referring to FIG. 2, the third member 116 and the fluid inlet body portion 100a may include a plurality of axially-aligned passages 116p and 100ap. The axially-aligned passages 116p and 100ap receive a plurality of fasteners 120 that removably-attaches the fluid outlet body portion 100b to the fluid inlet body portion 100a.

Referring to FIGS. 8A-8B, upon attachment of the fluid outlet body portion 100b to the fluid inlet body portion 100a with the plurality of fasteners 120, the first member 112 and the second member 114 are contained by the fluid inlet body portion 100a and the third member 116. In some instances, the fluid inlet body portion 100a may define a recessed portion $100a_R$, and, the third member 116 may define a first recessed portion, $116_{S1}$ that collectively defines a lower cavity 122 that contains the first member 112. In some examples, the first member 112 may define a recessed portion $112_S$, and, the third member 116 may define a second recessed portion, $116_{R2}$ that collectively defines an intermediate cavity 124 that contains second member 114. In some examples, the third member 116 may define a third recessed portion, $116_{S3}$ that defines an upper cavity 126 that contains fourth member 118 and a proximal end portion of the fluid output conduit 32.

Referring to FIG. 2, one or more leg portions 128 may be connected to the fluid inlet body portion 100a for supporting the fluid inlet body portion 100a upon an underlying ground surface, G. Each leg portion of the one or more leg portions 128 may include one or more fastener passages 130 that are aligned with one or more corresponding fastener passages 132 (see also, e.g., FIGS. 2A-2B and 7) formed in, for example, the third side surface 102c and the fourth side surface 102d in order to permit, for example, one or more fasteners 134 to connect the one or more leg portions 128 to the fluid inlet body portion 100a.

Referring to FIGS. 7 and 8A-8B, an exemplary system 10 may include four controlled flow cavitation devices $75_1$, $75_2$, $75_3$, $75_4$. The four controlled flow cavitation devices may be defined by: a first controlled flow cavitation device $75_1$, a second controlled flow cavitation device $75_2$, a third controlled flow cavitation device $75_3$ and a fourth controlled flow cavitation device $75_4$.

As described above, each diameter, $D_{66-S}$, formed by the distal opening $70_1$, $70_2$, $70_3$, $70_n$ of each nozzle $58_1$, $58_2$, $58_3$, $58_4$ yields a different flow rate of the fluid, $F_1$-$F_4$, that is directed into the fluid mixing and crystallization chamber 22 formed by the fluid receiver 14; therefore, in some instances, a user may select four unique nozzles $58_1$, $58_2$, $58_3$, $58_4$ having four unique diameters, $D_{66-S}$, that may structurally independently control different flow rates of the fluids, $F_1$-$F_4$ (e.g., solvents and/or anti-solvents), carried through the four controlled flow cavitation devices $75_1$, $75_2$, $75_3$, $75_4$. In an example, the first nozzle $58_1$ of the first controlled flow cavitation device $75_1$ may include a diameter, $D_{66-S}$, equal to approximately about 0.004", and, the second nozzle $58_2$ of the second controlled flow cavitation device $75_2$ may include a diameter, $D_{66-S}$, equal to approximately about 0.008", and, the third nozzle $58_3$ of the third controlled flow cavitation device $75_3$ may include a diameter, $D_{66\text{-}S}$, equal to approximately about 0.006", and, the fourth nozzle $58_4$ of the fourth controlled flow cavitation device $75_4$ may include a diameter, $D_{66\text{-}S}$, equal to approximately about 0.008". Within the above described exemplary diameter, $D_{66\text{-}S}$, parameters, each nozzle $58_1$, $58_2$, $58_3$, $58_4$ can be utilized to crystallize various types of chemical compounds; because each nozzle $58_1$, $58_2$, $58_3$, $58_4$ is removably-disposed within the substantially cylindrically-shaped counter bore 56 formed in the distal end 42 of the substantially cylindrically-shaped body 38 of each distal end portion 36, each nozzle $58_1$, $58_2$, $58_3$, $58_4$ can be replaced with a nozzle $58_1$, $58_2$, $58_3$, $58_4$ having a desired diameter, $D_{66\text{-}S}$, for crystalizing a particular chemical compound.

The distal end 18 (that may be formed by, for example, the distal ends 42, 64) of each of the four controlled flow cavitation devices $75_1$, $75_2$, $75_3$, $75_n$ is disposed within a corresponding fluid inlet port $20_1$-$20_4$ of a plurality of fluid inlet ports 20 formed by the fluid receiver 14; the plurality of fluid inlet ports 20 are defined by (and as described above at FIGS. 2, 2A-2B and 3A-3B): a first fluid inlet port $20_1$, a second fluid inlet port $20_2$, a third fluid inlet port $20_3$ and a fourth fluid inlet port $20_4$.

After disposing distal end 18 of each of the four controlled flow cavitation devices $75_1$, $75_2$, $75_3$, $75_n$ within the corresponding fluid inlet port $20_1$-$20_4$ of the plurality of fluid inlet ports 20 formed by the fluid receiver 14, the system 10 may be actuated by, for example, activating the computing processor 28. The computing processor 28 may then send a signal to each pump $24_1$-$24_n$ of the plurality of pumps 24 such that the computing processor 28 may be programmed to selectively control the speed of each pump $24_1$-$24_n$ in order to regulate an amount of each of the four fluids, $F_1$-$F_4$, being supplied to the fluid mixing and crystallization chamber 22 by the first fluid input conduit $12_1$, the second fluid input conduit $12_2$, the third fluid input conduit $12_3$ and the fourth fluid input conduit $12_4$.

When at least three of the four fluids, $F_1$-$F_4$, arrive at the fluid mixing and crystallization chamber 22, the at least three of the four fluids, $F_1$-$F_4$, converge upon the single spatial coordinate, X—Y—Z, within the fluid mixing and crystallization chamber 22 to form the processed fluid, P. By permitting the four fluids, $F_1$-$F_4$, to converge and impinge upon one another at the single spatial coordinate, X—Y—Z, the processed fluid, P, is formed at a very high level of super-saturation; as a result, crystallization of the processed fluid, P, occurs rapidly within a small mixing zone at the single spatial coordinate, X—Y—Z, of the four streams formed by each of the first fluid, $F_1$, the second fluid, $F_2$, the third fluid, $F_3$, and the fourth fluid, $F_4$.

The speed of each pump $24_1$-$24_n$ of the plurality of pumps 24 is sufficient to create a downstream fluid force behind the four fluids, $F_1$-$F_4$, within the fluid mixing and crystallization chamber 22 in order to urge the processed fluid, P, out of the fluid mixing and crystallization chamber 22 and into the outlet port 30 formed by the fluid receiver 14. The downstream fluid force may further urge the processed fluid, P, out of the outlet port 30 and into the fluid output conduit 32 that is fluidly-connected to the fluid outlet port 30, via the fluid outlet body portion 100b, for transporting the processed fluid, P, from the fluid outlet port 30 and to the processed fluid reservoir 34 that received the processed fluid, P, from the fluid receiver 14.

In some instances, the computing resource 28 may operate the plurality of pumps 24 for continuous processing in a batch-wise fashion. Continuous processing may afford two advantages: (1) the same amount of fluids, $F_1$-$F_4$, supplied to the fluid receiver 14 may be crystallized in significantly less volume by continuous processing than would be possible by using a batch method, and (2) continuous processing enhances reproducibility of results because all the fluids, $F_1$-$F_4$, may crystallize under uniform conditions.

Figure 10:
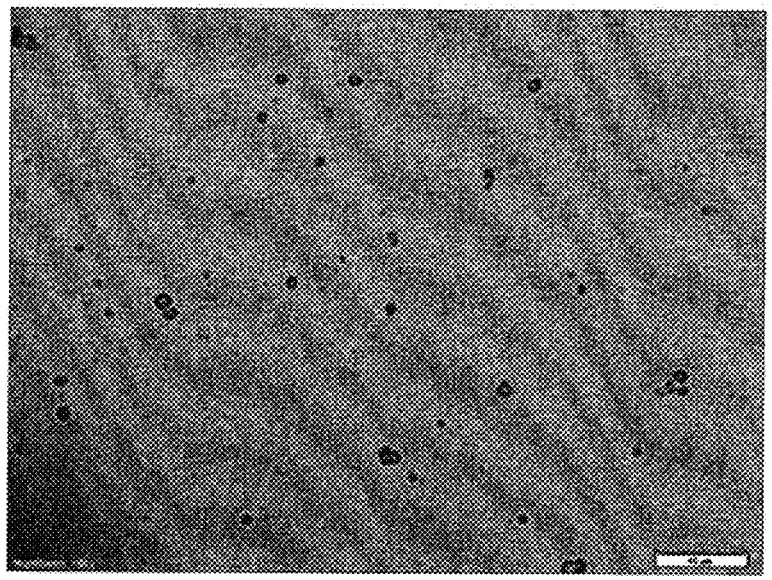
FIG. 10 illustrates an exemplary photomicrograph of crystals of paracetamol at 100 magnification viewed through a light microscope.
Figure 11:
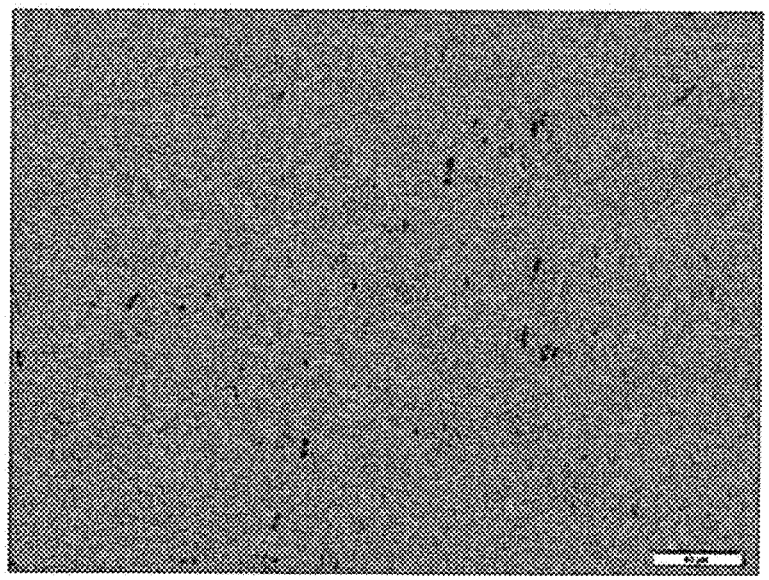
FIG. 11 illustrates an exemplary photomicrograph of crystals of carbamazepine at 100 magnification viewed through a light microscope.
Figure 12:
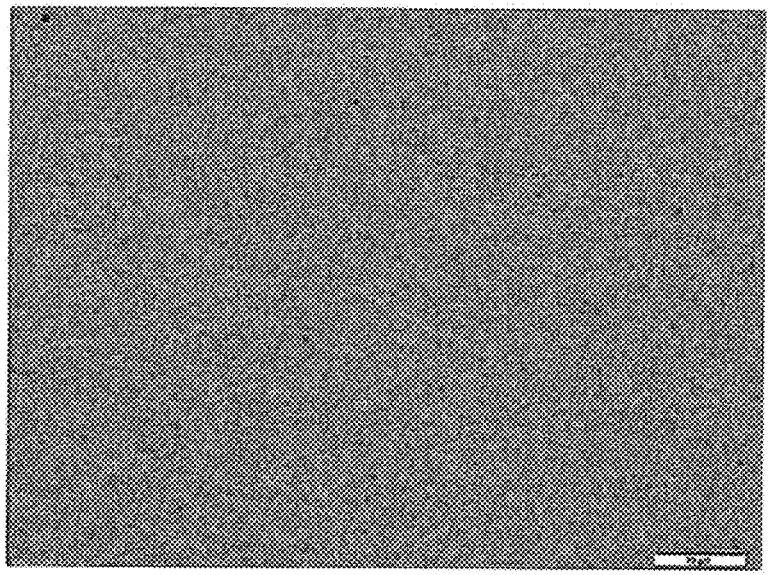
FIG. 12 illustrates an exemplary photomicrograph of crystals of ketoprofen at 100 magnification viewed through a light microscope.
Figure 13:
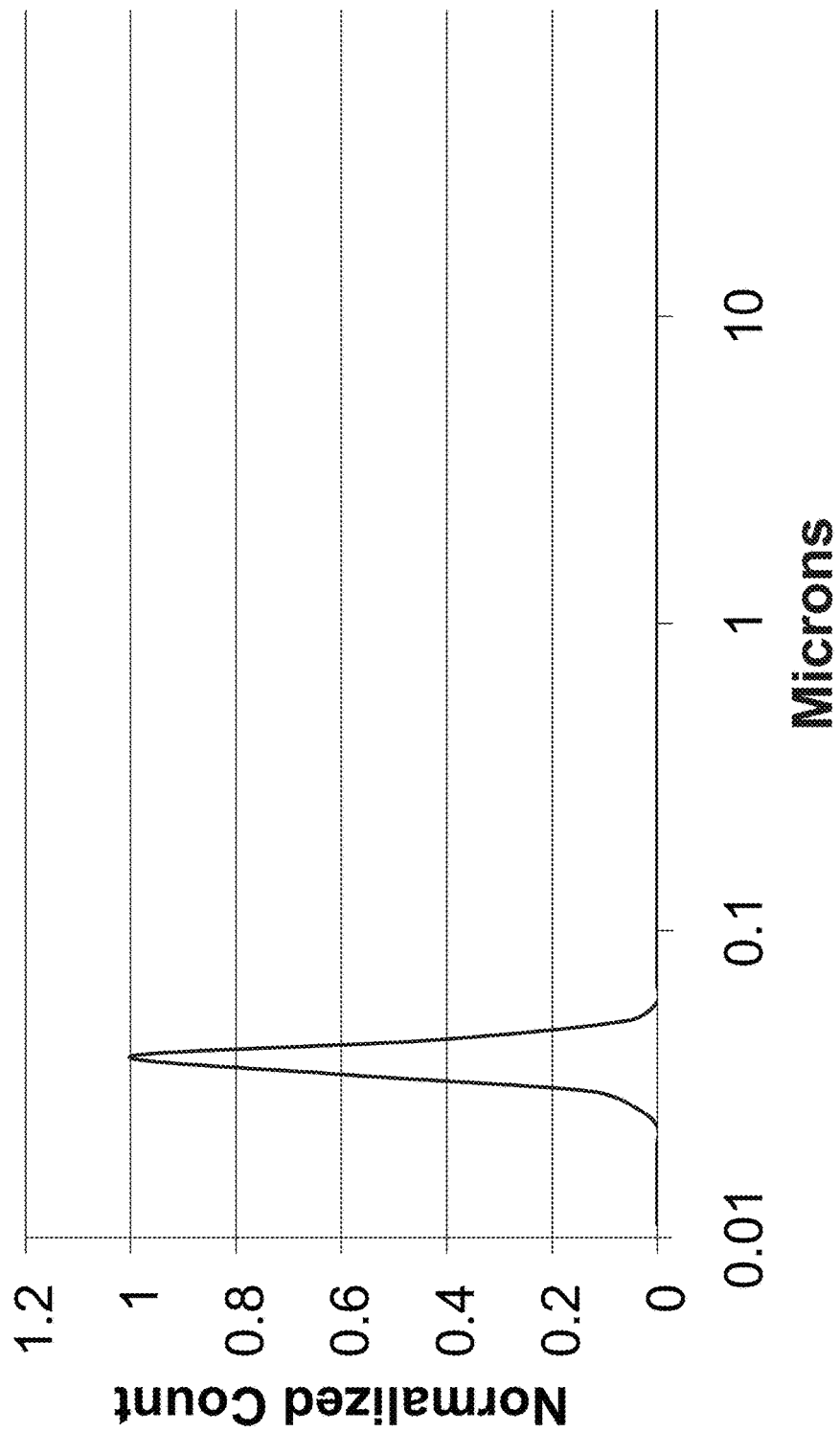
FIG. 13 is a graph illustrating the particle sizes and distributions of itraconazole.
Figure 14:
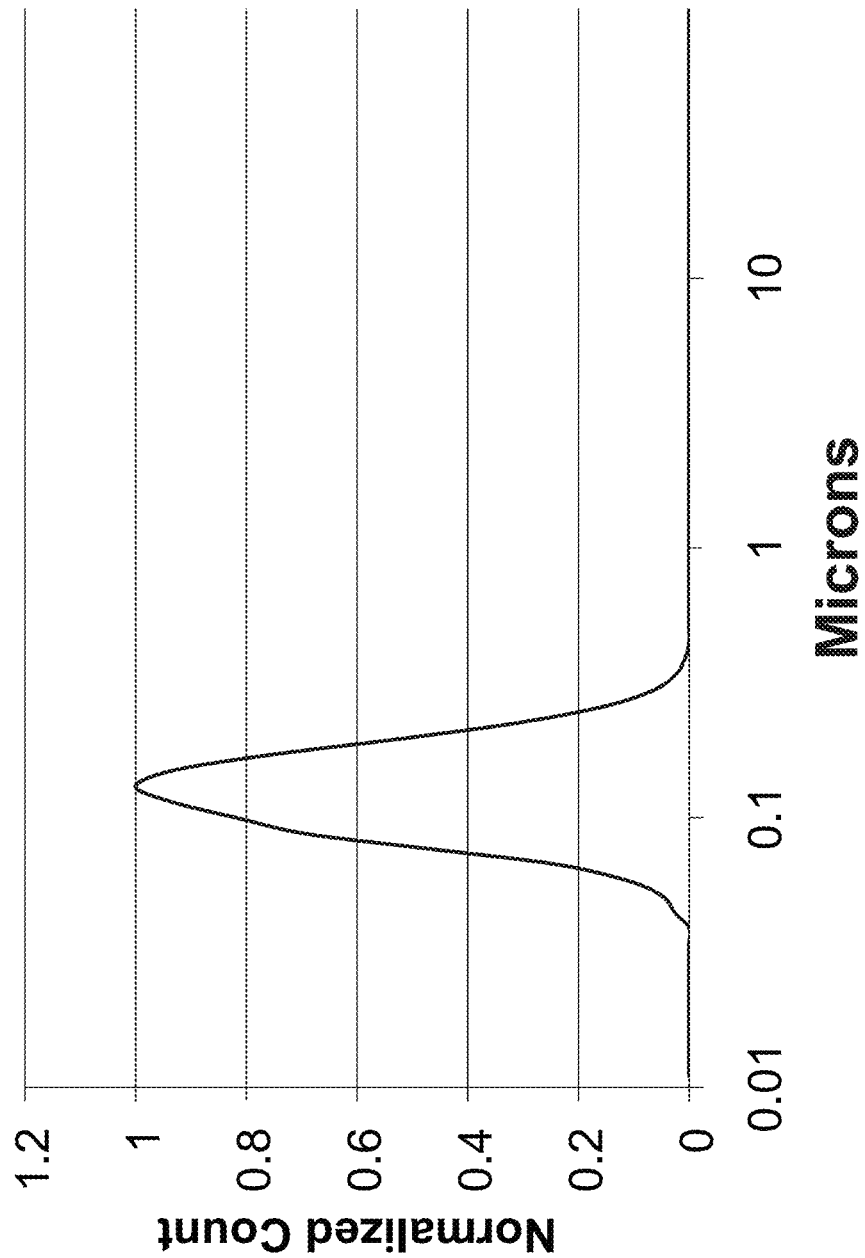
FIG. 14 is a graph illustrating the particle sizes and distributions of atorvastatin.
Figure 15:
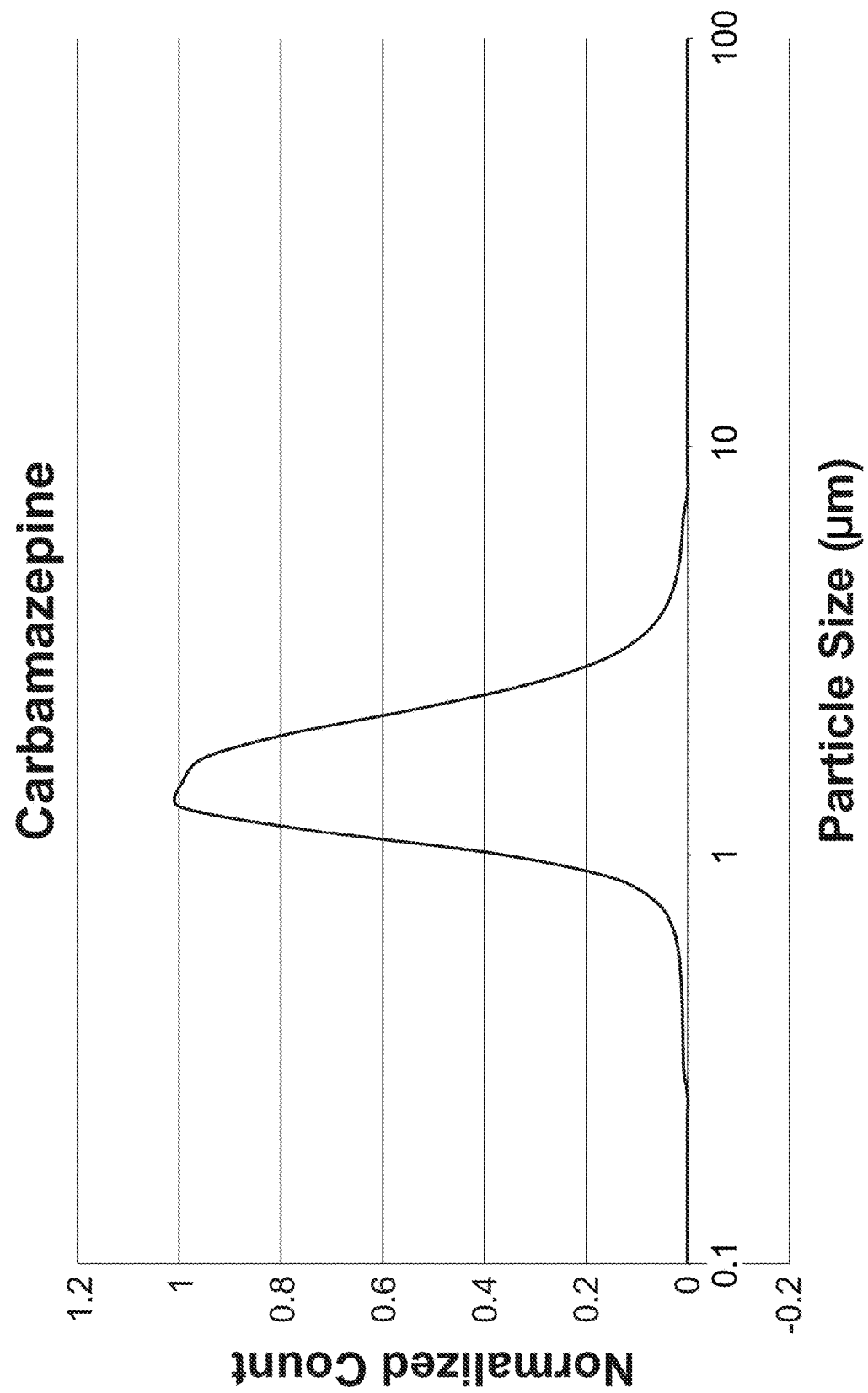
FIG. 15 is a graph illustrating the particle sizes and distributions of carbamazepine.
Figure 16:
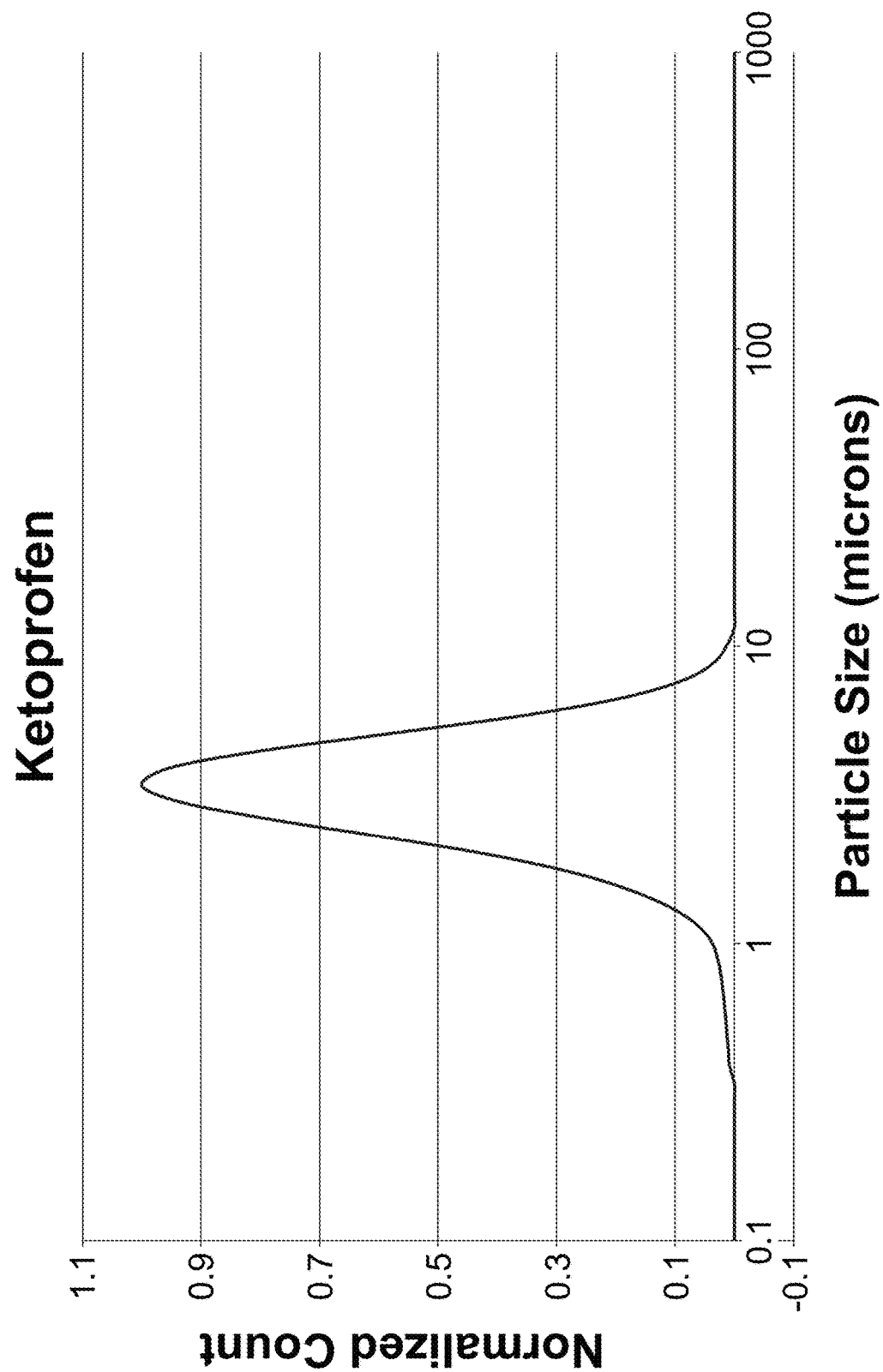
FIG. 16 is a graph illustrating the particle sizes and distributions of ketoprofen.
Figure 17:
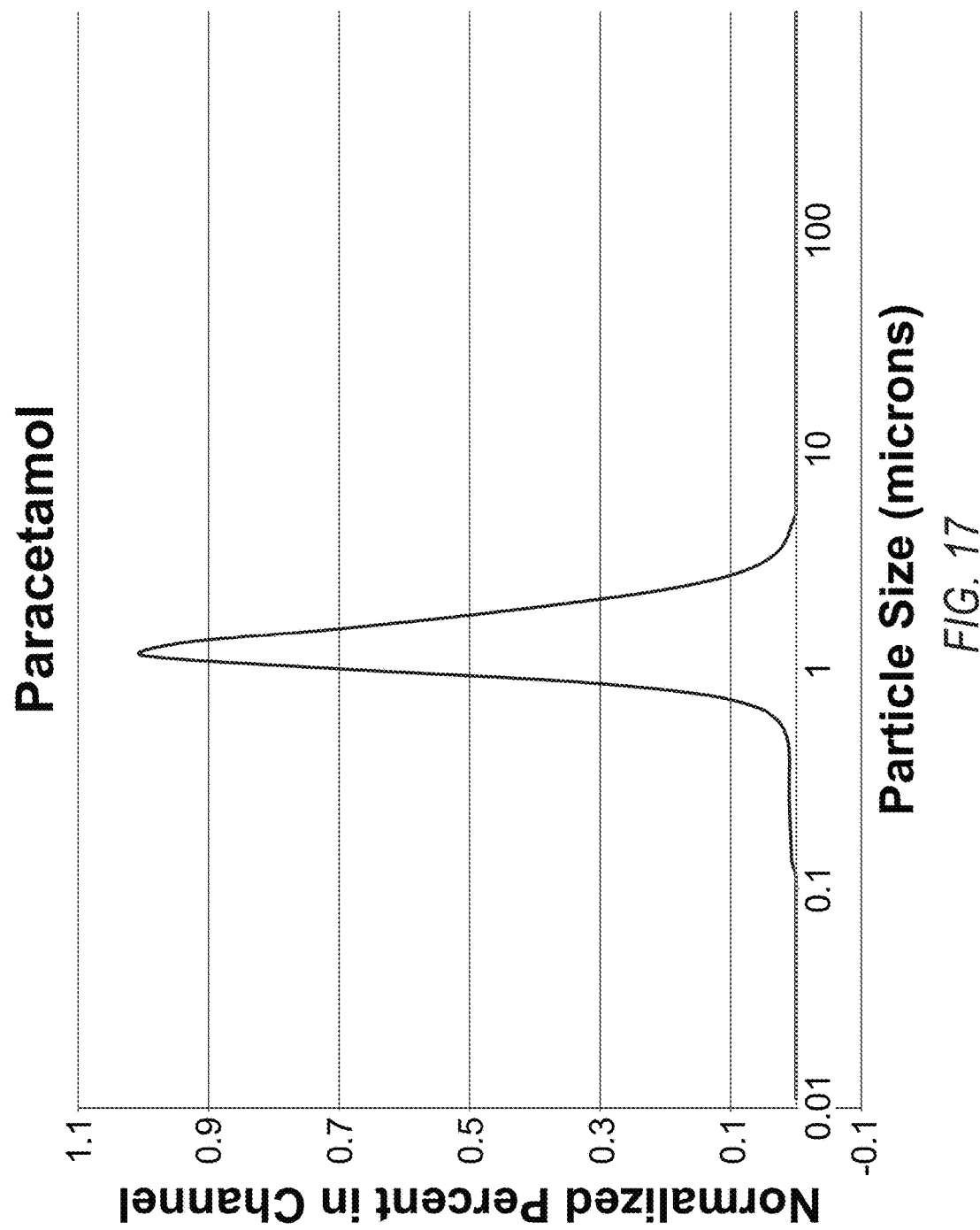
FIG. 17 is a graph illustrating the particle sizes and distributions of paracetamol.

Customized crystallization of, for example, pharmaceuticals or fine chemical compounds may be achieved via a process using the system 10. Referring to FIG. 9, the system 10 is capable of producing different particle sizes of a molecule with narrow distributions to provide a desired processed fluid, P. Further, as shown in FIGS. 10-12, the system 10 may produce more uniform and smaller crystals.

Referring back to FIG. 1, one or more of the fluids, $F_1$-$F_n$, may be a "feed solution" in which a compound to be crystallized within the fluid mixing and crystallization chamber 22 is substantially dissolved in a suitable solvent or combination of one or more solvents. Further, one or more of the fluids, $F_1$-$F_n$, may be one or more anti-solvents; the term "anti-solvent" may be refer to a suitable solvent or combination of one or more solvents that causes processed fluid, P, to crystallize or precipitate. An anti-solvent may be typically miscible with the solvent of a feed solution, whereas a processed fluid, P, to be crystallized is sparingly soluble in it.

In some embodiments, a compound to be crystallized may be in the range of a 5%-25% concentration. In other embodiments, a compound to be crystallized may be at a concentration as low as 1% or as high as at 30%. In one embodiment, the concentration is approximately 7%. Suitable solvents and anti-solvents include, but are not limited to: water, FDA Class 3 solvents; Acetic acid, Acetone, Anisole, 1-Butanol, 2-Butanol, Butyl acetate, tert-Butylmethyl ether, Cumene, Dimethyl sulfoxide, Ethanol, Ethyl acetate, Ethyl ether, Ethyl formate, Formic acid, Heptane, Isobutyl acetate, Isopropyl acetate, Methyl acetate, 3-Methyl-1-butanol, Methylethyl ketone, Methylisobutyl ketone, 2-Methyl-1-propanol, Pentane, 1-Pentanol, 1-Propanol, 2-Propanol, Propyl acetate, FDA Class 2 solvents; Acetonitrile, Chlorobenzene, Chloroform, Cyclohexane, 1,2-Dichloroethene, Dichloromethane, 1,2-Dimethoxyethane, N,N-Dimethylacetamide, N,N-Dimethylformamide, 1,4-Dioxane, 2-Ethoxyethanol, Ethyleneglycol, Formamide, Hexane, Methanol, 2-Methoxyethanol, Methylbutyl ketone, Methylcyclohexane, N-Methylpyrrolidone, Nitromethane, Pyridine, Sulfolane, Tetrahydrofuran, Tetralin, Toluene, 1,1,2-Trichloroethene, Xylene.

With continued reference to FIG. 1, one or more of the fluids, $F_1$-$F_n$, may be a suitable surfactant. Alternatively, one or more surfactants may be added as part of a premix with one or more of the fluids, $F_1$-$F_n$. Thus, the feed solution and one or all of anti-solvents may contain a surfactant. In some embodiments, the surfactant may be an emulsifying surfactant which is soluble in the feed solution and insoluble in the anti-solvent. A surfactant and a compound to be crystallized may be dissolved together in the process of the present invention. In a preferred embodiment, soy lecithin may be the surfactant. In some embodiments, a compatible emulsifying surfactant may also be used in the anti-solvent. For example, if tetrahydrofuran is the solvent of a feed solution, and the surfactant in the solvent is sobitan monooleate, then an appropriate surfactant in the anti-solvent (such as water) may be selected from the polysorbate series. Generally, suitable surfactants include, but are not limited to: gelatin, casein, lecithin, gum acacia, cholesterol, steric acid, benzalkonium chloride, calcium stearate, glycerol monostearate, cetostearyl alcohol, sorbitan esters, polyoxyethylene alkyl esters, polyoxyethylene castor oil derivatives, polyoxyethylene sorbitan fatty acid esters, polyethylene glycols, polyoxyethylene stearate, sodium dodecylsulfate, hydroxyl propylcellulose, polyvinylpyrrolidone and polyvinyl alcohols.

In some embodiments, the computing resource 28 may operate each pump $24_1$-$24_n$ of the plurality of pumps 24 at different speeds; therefore the solvents and anti-solvents may be pumped into the fluid mixing and crystallization chamber 22 at different rates. In some instances, when the computing resource 28 operates each pump $24_1$-$24_n$ of the plurality of pumps 24 at different speeds, a pressure difference of each fluid, $F_1$-$F_n$, with their respective fluid input conduit $12_1$-$12_n$ may be approximately 1500 psi. The difference in ranges of pressures may be between about 50 psi to 30,000 psi. Higher pressures may be utilized in order to influence the particle size distribution and to affect an increase in production rate of the processed fluid, P. Pressure also can be used to add asymmetry to the system 10.

Flow rate of the streams of the fluid, $F_1$-$F_n$, may be proportional to the square root of the pressure. Flow rates of the streams of the fluid, $F_1$-$F_n$, may dictate the kinetics of crystallization (i.e., particle size and uniformity). As described above, in some instances, the flow rate of the streams of the fluid, $F_1$-$F_n$, may also be controlled by the diameter, $D_{66-S}$, of each selected nozzle $58_1$, $58_2$, $58_3$, $58_n$. In some instances, flow rates of the fluid, $F_1$-$F_n$, toward the fluid mixing and crystallization chamber 22 may range from about 50 ml/min to 15 l/min. In some examples, one of the selected nozzles $58_1$, $58_2$, $58_3$, $58_n$ may include a low flow rate and the remainder of the selected nozzles $58_1$, $58_2$, $58_3$, $58_n$ may include a high flow rate; for example, a feed solution, $F_1$, may enter the fluid mixing and crystallization chamber 22 through a diameter, $D_{66-S}$, of a selected nozzle $58_1$ that is equal to approximately 0.004" and the anti-solvents, $F_2$-$F_n$, may enter fluid mixing and crystallization chamber 22 through diameters, $D_{66-S}$, of selected nozzles $58_2$, $58_2$, $58_3$ that are approximately equal to for example, 0.008", 0.006" and 0.008", with one or of the 0.008" diameters, $D_{66-S}$, opposing the 0.004" diameter, $D_{66-S}$. Such an exemplary configuration may provide asymmetry leading to nucleation of a low energy polymorph (i.e. a very stable polymorph).

In some example, the flow rate may be controlled by the power of the plurality of pumps 24. Further, a maximum practical flow rate may be determined by the final concentration of a compound in the anti-solvent. Yet even further, the solvent and anti-solvent may be removed to isolate the particles; as such, if the concentration of a compound in the final liquid, P, is below about 1% then significant amount energy may be utilized to remove the liquid. Conversely, if there is too little liquid (i.e., the concentration of a compound to be crystallized is higher than about 20%), then there may be too much agglomeration.

In some instances, the temperature of the fluids, $F_1$-$F_n$, may be varied to allow for super-saturation of the compound, P. For example, when a compound, P, is only modestly soluble in a solvent, the temperature of one or more of the fluids, $F_1$-$F_n$, might be increased (e.g., by, e.g., a heat exchanger, not shown) to allow for higher loading. In some examples, fluid temperatures may range from below room temperature to about 60° C., depending on the compound, P, to be crystallized. If a fluid temperature is too high, the high fluid temperature may break down a compound to be crystallized, whereas, conversely, a too low fluid temperature may limit the concentration of the compound in the solvent. In some embodiments, when the fluid temperature of the solvent is high, the fluid temperature of the anti-solvent is low; for example, when water is used as an anti-solvent, the temperature for the water may be about 1° C. When an organic solvent is used, the organic solvent may be cooled down to as low as the lowest freezing point of the solvent or anti-solvent.

The system 10 may enable the production of customized particle sizes. For example, the system 10 may form crystals in a range from about 10 nanometers to 90 microns.

Just as importantly as desirable small particle sizes is uniformity of particle size distributions (i.e., described by "D values"). D values of "D10", "D50" and "D90" may be used to represent the midpoint and range of particle sizes of a given sample. The D10 particle size is the diameter at which 10% of a sample's mass is comprised of smaller particles. The D50 is the "mass median diameter" as it divides the sample equally by mass. The D90 particle size is the diameter at which 90% of a sample's mass is comprised of smaller particles.

System 10 of the present invention enables the production of customized particles within a narrow range of particle sizes. A common value used to express the uniformity of particle size distribution is the "span". The span is a measure of how wide of a spectrum of particle sizes is produced. A system with a low relative span is desirable as it will produce more uniform distribution of particle sizes. Span can be calculated with the equation below:

$$\text{Span} = (D_{90} - D_{10})/D_{50}.$$

The term "compounds", "pharmaceutical compounds", or "fine chemical compounds" should be construed in their broadest sense. These terms generally refer to organic compounds containing carbon atoms and usually also contains hydrogen atoms. Very often organic compounds also contain oxygen, nitrogen or sulfur atoms. Pharmaceutical compounds that can be crystallized according to the present invention include, but are not limited to, anabolic steroids, analeptics, analgesics, anesthetics, antacids, anti-arrthymics, anti-asthmatics, antibiotics, anti-cariogenics, anticoagulants, anticolonergics, anticonvulsants, antidepressants, antidiabetics, antidiarrheals, anti-emetics, anti-epileptics, antifungals, antihelmintics, antihemorrhoidals, antihistamines, anti-hormones, antihypertensives, anti-hypotensives, anti-inflammatories, antimuscarinics, antimycotics, antineoplastics, anti-obesity drugs, antiplaque agents, anti-protozoals, antipsychotics, antiseptics, anti-spasmotics, anti-thrombics, antitussives, antivirals, anxiolytics, astringents, beta-adrenergic receptor blocking drugs, bile acids, breath fresheners, bronchospasmolytic drugs, bronchodilators, calcium channel blockers, cardiac glycosides, contraceptives, corticosteriods, decongestants, diagnostics, digestives, diuretics, dopaminergics, electrolytes, emetics, expectorants, haemostatic drugs, hormones, hormone replacement therapy drugs, hypnotics, hypoglycemic drugs, immunosuppressants, impotence drugs, laxatives, lipid regulators, mucolytics, muscle relaxants, non-steroidal anti-inflammatories, nutraceuticals, pain relievers, parasympathicolytics, parasympathicomimetics, prostagladins, psychostimulants, psychotropics, sedatives, sex steroids, spasmolytics, steroids, stimulants, sulfonamides, sympath icolytics, sympathicomimetics, sympathomimetics, thyreomimetics, thyreostatic drugs, vasodialators, vitamins, xanthines, and mixtures thereof.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The following examples are provided for the purpose of illustrating the present invention and should not be construed as being a limitation on the scope or spirit of the present invention. It should be understood that there may be other embodiments which fall within the spirit and scope of the invention as defined by the claims appended hereto.

Example 1 Crystallization of paracetamol
(N-(4-hydroxyphenyl)ethanamide)

Two grams of Paracetomol was dissolved in 100 grams of ethanol. Two grams of Soy Lecithin was dissolved in 50 grams of tetrahydrofuran (THF). The two solutions were combined and heated to 60° C. The solution was added to the input hopper of a dual piston pump $24_1$. The pump $24_1$ was fed into fluid input conduit $12_1$ of the crystallization chamber 22 through a 0.006" opening $70_1$ of a nozzle $58_1$. Heptane, at 10° C. was fed into fluid input conduits $12_2$, $12_3$ and $12_4$ through 0.006", 0.008" and 0.008" openings $70_2$, $70_3$, and $70_4$ of nozzles $58_2$, $58_3$, and $58_4$ respectively by an identical piston pump $24_2$. The pressure on both pumps $24_1$ and $24_2$ was adjusted to 1000 psi. The mixed streams exited through fluid output conduit 32 and into fluid reservoir 34 containing approximately 100 ml of heptane. Approximately, the first third and last third of the mixture were discarded and only the central third collected in fluid reservoir 34. The final solution was sampled and the particle size was measured, in heptane, using a Horiba L950 particle size analyzer. The median particle size was about 1.3 microns. The Span was about 0.901.

Example 2 Crystallization of carbamazapine
(5H-dibenzo[b,f]azepine-5-carboxamide)

Two grams of Carbamazepine was dissolved in 100 grams of ethanol. Two grams of Soy Lecithin was dissolved in 50 grams of THF. The two solutions were combined and heated to 60° C. The solution was added to the input hopper of a dual piston pump $24_1$. The pump $24_1$ was fed into fluid input conduit $12_1$ of the crystallization chamber 22 through a 0.004" opening $70_1$ of a nozzle $58_1$. Heptane, at 10° C. was fed into fluid input conduits $12_2$, $12_3$ and $12_4$ through 0.006", 0.007" and 0.007" openings $70_2$, $70_3$, and $70_4$ of nozzles $58_2$, $58_3$, and $58_4$ respectively by an identical piston pump $24_2$. The pressure on both pumps $24_1$ and $24_2$ was adjusted to 1500 psi. The mixed streams exited through fluid output conduit 32 and into fluid reservoir 34 containing approximately 100 ml of heptane. Approximately, the first third and last third of the mixture were discarded and only the central third collected in fluid reservoir 34. The final solution was sampled and the particle size was measured, in heptane, using a Horiba L950 particle size analyzer. The median particle size was about 1.5 microns. The Span was about 0.916.

Example 3 Crystallization of ketoprofen
((RS)-2-(3-benzoylphenyl)propanoic acid)

Two grams of Ketoprofen was dissolved in 100 grams of DMSO. Two grams of Sorbitan Monostearate was dissolved in 50 grams of THF. The two solutions were combined and heated to 60° C. The solution was added to the input hopper of a dual piston pump $24_1$. The pump $24_1$ was fed into fluid input conduits $12_1$ of the crystallization chamber 22 through a 0.004" opening $70_1$ of a nozzle $58_1$. DI water with 0.1% Polysorbate 20, at 5° C. was fed into fluid input conduits $12_2$, $12_3$ and $12_4$ through 0.006", 0.008" and 0.008" openings $70_2$, $70_3$, and $70_4$ of nozzles $58_2$, $58_3$, and $58_4$ respectively by an identical piston pump $24_2$. The pressure on both pumps $24_1$ and $24_2$ was adjusted to 1500 psi. The mixed streams exited through fluid output conduit 32 and into fluid reservoir 34 containing approximately 100 ml of distilled water (DI) water containing 0.1% Polysorbate 20. Approximately, the first third and last third of the mixture were discarded and only the central third collected in fluid reservoir 34. The final solution was sampled and the particle size was measured, in DI water, using a Horiba L950 particle size analyzer. The median particle size was about 3.1 microns. The Span was about 1.078.

Example 4 Crystallization of atorvastatin (3R,5R)-
7-[2-(4-fluorophenyl)-3-phenyl-4-(phenylcarbam-
oyl)-5-propan-2-ylpyrrol-1-yl]-3,5-dihydroxyhep-
tanoic acid)

Five grams of Atorvastatin was dissolved in 132 grams of dimethyl sulfoxide. Five grams of Soy Lecithin was dissolved in 68 grams of tetrahydrofuran. The two solutions were combined and heated to 60° C. The solution was added to a fluid inlet port hopper of a dual piston pump $24_1$. The pump $24_1$ was fed into fluid input conduits $12_1$ of the crystallization chamber 22 through a 0.004" opening $70_1$ of a nozzle $58_1$. DI water with 0.1% hydroxypropyl methylcellulose (HPMC), at 5° C. was fed into fluid input conduits $12_2$, $12_3$ and $12_4$ through 0.008", 0.010" and 0.008" openings $70_2$, $70_3$, and $70_4$ of nozzles $58_2$, $58_3$, and $58_4$ respectively by an identical piston pump $24_2$. The pressure on both pumps $24_1$ and $24_2$ was adjusted to 500 psi. The mixed streams exited through a 0.020" fluid output conduit 32 and into fluid reservoir 34 containing approximately 100 ml of DI water containing 0.1% HPMC. Approximately, the first third and last third of the mixture were discarded and only the central third collected in fluid reservoir 34. The final solution was sampled and the particle size was measured, in DI water, using a Horiba L950 particle size analyzer. The median particle size was about 126 nanometers (0.126 microns). The Span was about 0.99.

Example 5 Crystallization of itraconazole (2R,4S)-rel-1-(butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-1H-1,2,4-triazol-5-one Two grams of Itraconazole, two grams of Soy Lecithin and two grams of Sorbitan Monostearate were dissolved in 100 grams of tetrahydrofuran. The solution was heated to 60° C. The solution was added to a fluid inlet port hopper of a dual piston pump $24_1$. The pump was fed into fluid input conduits $12_1$ of the crystallization chamber 22 through a 0.004" nozzle opening $70_1$ of a nozzle $58_1$. DI water, at 5° C. was fed into fluid input conduits $12_2$, $12_3$ and $12_4$ through 0.008", 0.008" and 0.004" openings $70_2$, $70_3$, and $70_4$ of nozzles $58_2$, $58_3$, and $58_4$ respectively by an identical piston pump $24_2$. The pressure on both pumps $24_1$ and $24_2$ was adjusted to 485 psi. The mixed streams exited through a 0.018" fluid output conduit 32 and into a receiving fluid reservoir 34 containing approximately 100 ml of DI water. Approximately, the first third and last third of the mixture were discarded and only the central third collected in fluid reservoir 34. The final solution was sampled and the particle size was measured, in DI water, using a Horiba L950 particle size analyzer. The median particle size was about 36 nanometers (0.036 microns). The Span was about 0.34.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A system, comprising:
    a fluid receiver defined by a cavitation crystallization chamber,
    three or more fluid input conduits, wherein each fluid input conduit is configured to direct a fluid into the cavitation crystallization chamber such that the fluids from the fluid input conduits converge on a single spatial coordinate (X—Y—Z) within the cavitation crystallization chamber, and
    a fluid outlet body portion.

2. The system of claim 1, wherein the fluid receiver is further defined by a first fluid inlet port, a second fluid inlet port, a third fluid inlet port, and a fourth fluid inlet port, wherein the first fluid inlet port and the second fluid inlet port are respectively formed in opposing side surfaces of the fluid receiver, wherein the third fluid inlet port and the fourth fluid inlet port are formed in a side surface connecting the opposing side surfaces.

3. The system of claim 2, wherein a first axis extends through the first fluid inlet port, wherein a second axis extends through the second fluid inlet port, wherein a third axis extends through the third fluid inlet port, wherein a fourth axis extends through the fourth fluid inlet port, wherein the first axis is offset from the second axis at a first angle, wherein the third axis is offset from the fourth axis at a second angle, wherein both of the first angle and the second angle are not equal to 90°, wherein both of the first angle and the second angle are not equal to 180°.

4. The system of claim 3, wherein the first angle ranges between about 120° and about 175°.

5. The system of claim 4, wherein the first angle is approximately equal to 150°.

6. The system of claim 3, wherein the second angle ranges between about 30° and about 85° degrees.

7. The system of claim 6, wherein the second angle is approximately equal to 60°.

8. The system of claim 1 further comprising: a processed fluid reservoir that is fluidly-connected to a distal end of the fluid output conduit.

9. The system of claim 1, wherein each of the three or more fluid input conduits includes: a proximal end that is respectively fluidly-connected to a fluid source of a plurality of fluid sources to permit the proximal end of each of the three or more fluid input conduits to respectively draw a fluid from each fluid source of the plurality of fluid sources, and a distal end that is respectively fluidly-connected to the cavitation crystallization chamber.

10. The system of claim 9, further comprising one or more pumps that are arranged downstream of each fluid input conduit of the three or more fluid input conduits.

11. The system of claim 10, wherein each fluid input conduit of the three or more fluid input conduits includes a check valve that is arranged downstream of the pump and upstream of the distal end of each fluid conduit of the three or more fluid input conduits.

12. The system of claim 10 further comprising: a computing resource that is communicatively-coupled to each pump and that controls an operating speed of each pump to therefore control a flow rate of each fluid that is drawn from each fluid source of the plurality of fluid sources.

13. The system of claim 9, wherein each fluid input conduit of the three or more fluid input conduits includes a distal end portion having a substantially cylindrically-shaped body that defines a proximal end and a distal end, wherein the distal end of the substantially cylindrically-shaped body forms a portion of the distal end of each fluid input conduit of the three or more fluid input conduits.

14. The system of claim 13, wherein the substantially cylindrically-shaped body of the distal end portion forms a passage that extends through an entire length of the substantially cylindrically-shaped body, wherein access to the passage is permitted by a proximal opening formed in the proximal end of the substantially cylindrically-shaped body and a distal opening formed in the distal end of the substantially cylindrically-shaped body.

15. The system of claim 14, wherein the proximal opening and a first substantially cylindrical inner surface of the substantially cylindrically-shaped body defines the passage to include a first diameter that extends through a majority of the length of the substantially cylindrically-shaped body, wherein the distal opening and a second substantially cylindrical inner surface of the substantially cylindrically-shaped body defines the passage to include a second diameter that extends through a minority of the length of the substantially cylindrically-shaped body, wherein a radial shoulder surface further defines the passage and connects the first substantially cylindrical inner surface to the second substantially cylindrical inner surface, wherein the second diameter is greater than the first diameter, wherein the second substantially cylindrical inner surface and the radial shoulder surface defines the passage to include a counter bore formed in the distal end of the substantially cylindrically-shaped body.

16. The system of claim 15 further comprising: a nozzle removably-disposed within a counter bore for removably-connecting the nozzle to the distal end of the distal end portion.

17. The system of claim 16, wherein the nozzle includes a body having a proximal end and a distal end wherein the distal end of the body of the nozzle and the distal end of the substantially cylindrically-shaped body of the distal end portion form the distal end of each fluid input conduit of the three or more fluid input conduits.

18. The system of claim 17, wherein the body of the nozzle forms a passage that extends through an entire length of the body wherein access to the passage is permitted by a proximal opening formed in the proximal end of the body of the nozzle and a distal opening formed in the distal end the body of the nozzle, wherein the passage is formed by a substantially conical inner surface defining a diameter that decreases along the length of the body of the nozzle such that the proximal opening defines the passage to include a first, larger diameter and the distal opening defines a second, smaller diameter.

19. The system of claim 18, wherein the second, smaller diameter formed by the distal opening of the nozzle ranges between about 0.001" to about 0.1".

20. A process for crystallization of the chemical compound comprising using the system of claim 1, wherein the chemical compound is a pharmaceutical compound.

21. The process of claim 20, wherein a first fluid of three or more fluids carried by a first fluid input conduit of the three or more fluid input conduits is a feed solution, wherein a second fluid, a third fluid, and a fourth fluid of the three or more fluids carried, respectively, by a second fluid input conduit, a third fluid input conduit, a fourth fluid input conduit of the three or more fluid input conduits are one or more anti-solvents.

22. The process of claim 21, wherein the feed solution comprises a compound to be crystallized and one or more solvents, wherein the compound is at a concentration in the solvent from about 1% to about 30%.

23. The process of claim 22, wherein the compound is at a concentration from about 5% to about 25%.

24. The process of claim 22, wherein the compound is at a concentration from about 10% to about 20%.

25. The process of claim 22, wherein the compound is at a concentration from about 7% to about 8%.

26. The process of claim 21, wherein the feed solution and anti-solvents are independently at a temperature in a range from about 0° to about 80°.

27. The process of claim 21, wherein the feed solution and anti-solvents are independently at a temperature in a range from about 25° to about 60°.

28. The process of claim 21, wherein the feed solution or anti-solvent independently comprises one or more surfactants.

29. The process of claim 28, wherein the surfactants is selected from the group consisting of gelatin, casein, lecithin, gum acacia, cholesterol, steric acid, benzalkonium chloride, calcium stearate, glycerol monostearate, cetostearyl alcohol, sorbitan esters, polyoxyethylene alkyl esters, polyoxyethylene castor oil derivatives, polyoxyethylene sorbitan fatty acid esters, polyethylene glycols, polyoxyethylene stearate, sodium dodecylsulfate, hydroxyl propylcellulose, polyvinylpyrrolidone and polyvinyl alcohols.

30. The process of claim 28, wherein the surfactants are emulsifying surfactants.

31. The process of claim 28, wherein the surfactant is soy lecithin.

32. The process of claim 21, wherein said feed solution and anti-solvents independently run at a flow rate in a range from about 50 ml/min to about 15 l/min.

33. A system, comprising:
   a fluid receiver defined by a cavitation crystallization chamber, a first fluid inlet port and a second fluid inlet port, wherein a first axis extends through the first fluid inlet port, wherein a second axis extends through the second fluid inlet port, wherein the first axis is offset from the second axis at a first angle, wherein the first angle is not equal to 90° and the first angle is not equal to 180°;
   two or more fluid input conduits, wherein each fluid input conduit is configured to direct a fluid into the cavitation crystallization chamber such that the fluids from the fluid input conduits converge on a single spatial coordinate (X—Y—Z) within the cavitation crystallization chamber, and
   a fluid outlet body portion.

* * * * *